United States Patent
Andros et al.

Patent Number: 5,842,175
Date of Patent: Nov. 24, 1998

[54] THERAPY SYSTEM

[75] Inventors: Todd Andros, Coral Gables; Alan Redmon, Stuart, both of Fla.

[73] Assignee: TherAssist Software, Inc., Coral Gables, Fla.

[21] Appl. No.: 431,121

[22] Filed: Apr. 28, 1995

[51] Int. Cl.⁶ .................................................. G06F 159/00
[52] U.S. Cl. .................................................. 705/3; 705/1
[58] Field of Search ................................. 395/202, 203, 395/208, 145; 235/379, 380; 707/530–531, 534, 539, 540; 704/1, 9; 705/2, 3

[56] References Cited

U.S. PATENT DOCUMENTS

| | | | |
|---|---|---|---|
| 4,642,769 | 2/1987 | Petrofsky | 364/415 |
| 4,839,822 | 6/1989 | Dormond et al. | 364/513 |
| 4,858,121 | 8/1989 | Barber et al. | 395/202 |
| 5,229,584 | 7/1993 | Erickson | 235/375 |
| 5,262,943 | 11/1993 | Thibaldo et al. | 395/140 |
| 5,359,509 | 10/1994 | Little et al. | 395/201 |
| 5,524,645 | 6/1996 | Wills | 128/898 |
| 5,583,758 | 12/1996 | McIlroy et al. | 395/202 |

OTHER PUBLICATIONS

Advertising and demonstration materials—Paradigm Technologies.
Advertising and demonstration materials—Precedent Systems, Inc.
Advertising and demonstration materials—Computer Notes.
Data Widgets™—Advertisements and Reviews.
PT Link Corporation, The Pathways Group, Inc.—Printed advertisement.

*Primary Examiner*—Frantzy Poinvil
*Attorney, Agent, or Firm*—Quarles & Brady

[57] ABSTRACT

A computer system and method for assisting the administration and monitoring of the therapy of patients includes the step of storing patient individual data records in a memory of a computer system. The patient data record for a selected patient is retrieved and updated in the memory of the computer system upon the arrival of the selected patient for a therapy activity. The computer system is operated to generate at least one therapy session input screen corresponding to the selected patient, the screen including treatments for the patient. Data is input into the therapy session input screen at least in part by the therapy provider selecting from lists of data. The selected data is recorded to provide a record of the patient activity during the therapy session.

40 Claims, 44 Drawing Sheets

Acme Physical Therapy
Patient Flow Sheet
Date: 03/07/1995

Patient Name: Berke, Frederick
Patient Number:

Therapist: Alvin A. Ponce de Leon
Referring Physician: Dr. Bruce Waxman
Problem Site: Spine - Lumbar, Hip - Left, Hip - Right, Foot/Ankle - Right, Hand - Right
Diagnosis: Spinal Stenosis, Lumbar Region(724.02)
Date of Birth:
Insurance: MediCare
Initial Visit: 11/13/1994
Total Visits: 12

Comment: patient had trouble with ice pack too cold pacemaker.

| Exercise/Modality Description | Plan for 03/07/1995 | 2/16/1995 | 1/27/1995 | 1/26/1995 |
|---|---|---|---|---|
| ADL training Hair Brush & teeth care | 3/10/0 | 3/10/0 | 3/10/5 | 3/10/15 |
| ADL training Box Carry | 3/10/5 | | | |
| Hot Pack Moist Heat | 25 | 25 | 25 | 25 |
| Cryotherapy Crushed ice | 8 | On Hold | On Hold | On Hold |
| Gait Training Cane/Walker | On Hold | 10 | On Hold | 25 |
| AROM adduction use cybex at seat height 12in | 3/10/50 | 3/10/50 | 3/10/50 | 3/10/50 |
| Isokinetics - Flexion/Extension BodyMaster Seat @4 | 3/10/5 | 3/10/5 | 3/10/5 | 3/10/5 |
| E-Stim attended Freq=15 | 15 | 15 | 15 | 15 |
| Biofeedback | 10 | 10 | 10 | 10 |
| Massage | On Hold | On Hold | On Hold | On Hold |
| AAROM adduction | 3/10/50 | 3/10/50 | 3/10/50 | 3/10/50 |
| ADL training | 3/10/50 | | | |

Goals: Decrease Pain, Decrease Muscle Spasm, Increase ROM, Increase Strength, Increase Postural Awareness Therapist: _____
Norma Morrision, PT0008739

FIG. 11

| Description | On Hold | Sets | Reps | Wt | Dur | Completed |
|---|---|---|---|---|---|---|
| Massage | No | 0 | 0 | 0 | 7 | Yes |
| Hot Pack | No | 0 | 0 | 0 | 25 | Yes |
| TENS | No | 0 | 0 | 0 | 10 | Yes |
| Kinetic Activities | No | 3 | 10 | 0 | 0 | Yes |
| Elect/Stimulation | No | 0 | 0 | 0 | 20 | Yes |

| Patient Complaint | Location | Site |
|---|---|---|
| Burning | Anterior | Elbow - Left |
| Coldness | Caudal | Elbow - Right |
| Heat | Cranial | Foot/Ankle - Left |
| Lack of Motion | Distal | Foot/Ankle - Right |
| Numbness | Dorsal | Hand - Left |
| Pain | Inferior | Hand - Right |
| Soreness | Lateral | Hip - Left |
| Spasm | Lateral Joint Line | Hip - Right |
| Stiffness | Medial | Knee - Left |

Note Text

Patient complains of lack of motion

| | Objective Finding | Initial | Today | Goal |
|---|---|---|---|---|
| 0 | AROM Knee extension | 12 | | 0 |
| 0 | AROM Knee flexion | 85 | | 150 |
| 0 | AROM Shoulder adduction Rt | 24 | | 40 |
| 0 | AROM Shoulder abduction Rt | 105 | | 170 |
| 0 | AROM Shoulder extension Rt | 30 | | 50 |

*Add or Delete Objective Findings for Ines Alvarez*

Objective Findings
- Adson Manuever
- Appley Compression
- Appley Distraction
- AROM Ankle dorsiflexion
- AROM Ankle eversion
- AROM Ankle inversion
- AROM Ankle Plantarflexion
- AROM Cervical backward bend
- AROM Cervical forward bend
- AROM Cervical Lf. rotation
- AROM Cervical Lf. side bend
- AROM Cervical Rt. rotation
- AROM Cervical Rt. side bend
- AROM Digit 2 DIP extension
- AROM Digit 2 DIP flexion
- AROM Digit 2 MCP Abduction
- AROM Digit 2 MCP Adduction

Objective Findings Selected
- MUSCLE SPASM
- AROM Lumbar extension
- AROM Lumbar flexion
- AROM Knee extension
- AROM Knee flexion
- Pain / Palpatation Scroll Up / Scroll Down / Remove Item / OK 744, 750, 746, 754

| | | | | 1020 | 1024 |
|---|---|---|---|---|---|
| 1004 | | | 1016 | | |

Progress Note for Inez Alvarez

| Subjective | Objective | Assessment | Plan | Status | Billing |

QuickBill | Billing Items Selected
--- | ---
<No Charge> | E_STIM (Unattended) 97014
ADL (Add) 97541 | Hot Pack 97010
ADL 97540 | Kinetic Activities 30min 97530
ADL Checkout (add) 97701 | Massage 97124
ADL Checkout (Init 30 min) | Range of Motion 95851
Biofeedback 90900 | E-STIM (Attended) 97118
Contrast Bath 97128 |
Cryotherapy 97010 | Insurance
Cybex retest 97752 | MedCard(IMP)
Dexamethazone 99070 |
E-STIM (Attended) 97118 |
E_STIM (Unattended) 97014 | Scroll Up
Eval (Add 15 min) 97721 |
FCA 97799 | Back | Next
Fluidotherapy 97039 | Scroll Down | About Note 80      1000      1026

Fig 27.

*IntegraCare*
Daily Note

| | |
|---|---|
| Date of Visit: | 1/10/95 |
| Patient Name: | Andros, Todd |
| Patient Number: | 13 |
| Diagnosis: | Limb pain(729.5), Pain Multiple Sites(719.49), Ankylosis/mult.sites(718.59) |
| Problem Site: | Shoulder - Left |
| Date of Birth: | 3/5/1959 |
| Physician: | Dr. Dan Sharkey |

*Subjective*   Patient complaining of headaches and soreness in the left shoulder.

*Objective*   Flow Chart for treatment administered

```
Objective Findings            Initial   Current   Goal
------------------            -------   -------   ----
Pain / Palpatation            Yes       Yes       No
AROM Shoulder flexion Rt      105       160       180
AROM Shoulder extension Rt    30        41        80
AROM Shoulder abduction Rt    105       155       170
AROM Shoulder adduction Rt    24        37        40
AROM Knee flexion             85        96        150
AROM Knee extension           12        3         0
```

Assessment   Progress is slow, but progessing.

Plan   Continue therapy as precribed for individual.

| <u>Billing Code</u> | <u>Billing Description</u> |
|---|---|
| 97124 | Massage 97124 |
| 64550 | TENS 64550 |
| 97128 | Ultrasound 97128 |
| 97530 | Kinetic Activities 30 min 97530 |

Therapist   _____
Norma C. Morrison, PT

FIG. 30

THERAPY SYSTEM

FIELD OF THE INVENTION

This invention relates generally to therapy for patients and customers, and more particularly to systems for administering and monitoring therapy.

BACKGROUND OF THE INVENTION

Therapy for patients includes a broad range of fields such as physical therapy, occupational therapy, brain therapy, speech therapy, chiropractic, exercise therapy, and the like. Each of these fields presents challenges to the therapy provider in administering and monitoring the therapy of many patients. The appointments for each patient must be coordinated with responsible therapy providers. Data concerning the patient background, diagnosis, and treatment plan must be available for use by the therapist. A treatment plan for the patient must be administered during the therapy session, and a report of the results should be generated. The collection and maintenance of so much data for so many patients creates a burden for therapy providers, which can adversely affect the quality of care that is given to the patient or customer. It is therefore desirable that a system be provided to administer, monitor, and report therapy on an efficient and accurate basis.

SUMMARY OF THE INVENTION

It is an object of the invention to provide systems for administering, monitoring, and reporting the results of therapy sessions.

It is another object of the invention to improve the quality of care given to patients during therapy sessions.

It is still another object of the invention to provide a system which will enable therapy providers to more easily perform their duties for many patients and customers in an effective and efficient manner.

These and other objects are accomplished by a system for administering, monitoring and reporting the results of therapy sessions in which a programmable computer is provided and at least one set of patient rehabilitation data is defined. A visual representation for at least some of the patient rehabilitation data is also defined and displayed on a computer screen. Means are provided to permit the therapy provider to select at least one of the visual representations. The selected representations are stored for further use by the therapist and/or for reporting the results of the therapy session.

Some of the patient rehabilitation data, or some of the visual representations for that data, can be displayed as a list. Data selected from the list becomes individual patient data that is particular to that patient for the therapy session. Context sensitive, predefined phrases are used to build sentences from the selection of the patient data. The phrases are stored with the patient data when the data is selected from the list. The therapy provider can thereby build a complete sentence record of the data.

The visual representations of the patient rehabilitation data preferably comprise symbols or abbreviations for the patient rehabilitation data such that the patient rehabilitation data can be stored upon the selection of the corresponding symbol or abbreviation. The selection is made by suitable computer structure such as a touch screen, mouse, computer pen, and/or alpha-numeric data entry device. Other data input devices could also be used. A selected patient data is preferably displayed in at least a partially blank text area on the computer screen.

In a preferred embodiment, at least one reception computer and at least one remote computer are provided. The remote computer can be networked to the reception computer, whereby patient rehabilitation data can be communicated between the computers. The reception computer is used to provide access to a list of patients. Selection of a patient name permits the retrieval from a computer memory of individual patient rehabilitation data for the patient, the overall patient record, which will typically include the names of therapy providers for the patient.

The patient rehabilitation data includes general data that is not specific to a particular patient, and data that is specific to individual patients. The general data includes the various choices for body location, patient symptoms, diagnosis, and the like, from which the therapy provider selects to create or change a patient record. The general data that is stored in the computer memory can be changed, depending on the type of therapy that is being administered and the particular wishes or requirements of the therapy clinic in which the system is operating. The patient specific data, or individual patient data, are the entries which have been made for the particular patient, both during the present therapy session and in previous therapy sessions, to create a patient record.

The patient rehabilitation data, both general data and individual data, is stored as data fields in the computer memory. The data fields are grouped as records, for example, data fields comprising different body parts would be grouped as a location record. The system produces forms, preferably as screens, which assist the therapy provider in selecting from the general patient data, and in inputting data collected during the therapy session, to create individual patient data. Individual patient data records are grouped together and stored as an overall patient record for that patient. All records comprise a patient rehabilitation data file for the system. The computer memory also stores program instruction files that are used to operate the system.

Each therapy provider is preferably provided with his or her own remote computer. Selection of the name of a therapy provider at the reception computer preferably retrieves the patient record and sends the record to the remote computer of the appropriate therapy provider. In a preferred embodiment, an indication at the remote computer is provided to the therapy provider that the patient has arrived for therapy.

The patient rehabilitation data preferably includes patient symptom data, which can further include complaint data describing the nature of the patient's complaint, and site data, describing the location on the body of the complaint. The site data can include data as to the particular body part, such as lateral and medial, and proximal and dorsal, location data.

Individual patient rehabilitation data records preferably includes several fields of data corresponding to patient identifying data, patient problem site, diagnosis, and treatment goals data. The program provides a form for entering such fields of data by the therapy provider. The individual patient rehabilitation data records preferably include a therapy treatment plan for the patient. The therapy treatment plan is preferably sent to a printer to produce a printed copy of the treatment plan for use by the therapy provider during the therapy session with the patient.

The treatment plan can be changed by the therapy provider. At least a portion of the representations can be displayed as a list of options in a portion of the computer screen. The therapy provider selects from the options, and the selected options are displayed in another portion of the computer screen. The options are selected from exercises, modalities, with predefined actions. The list of options can be edited by the therapy provider for the particular characteristics and status of the patient.

Individual patient rehabilitation data is taken during the therapy session, and entered as data fields by the therapy provider after the therapy session. These data fields comprise information to be entered in several different data records, which preferably include the patient's subjective, objective, assessment and plan data records (known as a "SOAP" note in the therapy industry) for the therapy session.

The patient rehabilitation data records preferably also includes patient status data records. The patient status data records can include individual patient condition, time remaining in therapy, and patient notes fields entered by the therapy provider.

After the therapy session has been completed, a portion of the individual patient rehabilitation data record entered during the therapy session is preferably sent to a printer to produce a printed report of the results of the therapy session. The patient status data record can be sent to a printer to produce a printed status report which can be forwarded to an attending physician or other person. The printing device can be a facsimile device, such that the report is transmitted to the physician.

Patient billing data can also be displayed as a list of options. The therapy provider can select from the list or table of options to generate an individual patient billing data record for the therapy session. Insurance carrier data for the patient can be provided to permit the selection of billing data appropriate for the carrier. The selected billing data for the therapy session can be sent to a data storage device, a printer, an electronic transmission device, and the like.

A method for operating a programmable computer to facilitate the rehabilitation of patients and the documentation of the rehabilitation includes an initial step of defining at least one field of patient rehabilitation data. Visual representations are defined for at least some of the patient rehabilitation data fields. These representations can be displayed on a computer screen. Means are provided for selecting the representations, and means responsive to the selection are provided for entering the data fields to create a record. The means for entering including displaying a numeric keypad on the computer screen for entering numerical patient data. A partially blank text entry area can be displayed on the computer screen for displaying text entered by the user on an alpha-numeric data entry device. In another data entering embodiment, predefined alternatives can be displayed in sequential fashion responsive to the selection, such that the user can continue the selection process until the desired alternative appears.

BRIEF DESCRIPTION OF THE DRAWINGS

There are shown in the drawings embodiments which are presently preferred, it being understood, however, that the invention is not limited to the precise arrangements and instrumentality's shown, wherein:

FIG. 11 is a depiction of a flow sheet.

FIG. 12 is a screen showing the work completed for the patient during a therapy session.

FIGS. 16a–d are progressive screens showing the construction of assessment notes from multiple tandem tables of data for the patient.

FIG. 18 is a screen showing the entering objective findings for the patient.

FIG. 19 is a screen showing the adding/deleting of objective findings.

FIG. 22 is a screen showing the modification of a treatment plan for a patient.

FIGS. 23 and 24 are progressive screens showing the entering of comments for individual exercises and modalities in the treatment plan and the overall comment for the patient.

FIG. 27 is a screen showing the selection of billing data for the therapy session.

FIG. 30 is an example of a patient report.

DETAILED DESCRIPTION OF THE PREFERRED EMBODIMENTS

The invention is suitable for performing therapy and patient rehabilitation in a variety of environments. Suitable environments include: physical therapy, occupational therapy, brain therapy, speech therapy, chiropractic, exercise therapy, and the like. The invention will be described with respect to physical therapy, but it should be understood that the principles described herein will be applicable to other environments with modification to the particular data that is utilized by each discipline.

Figure 1:
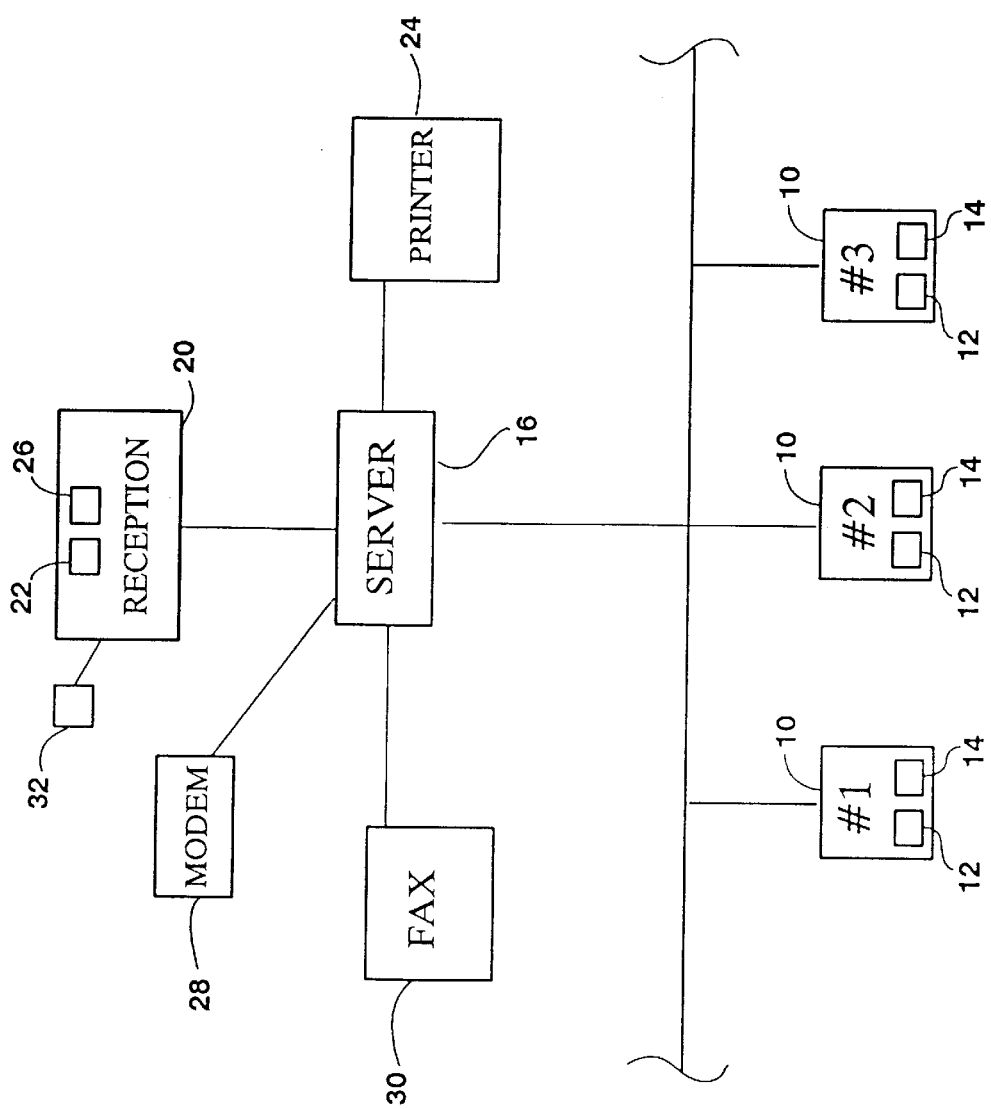
FIG. 1 is a schematic diagram of a system according to the invention.

A schematic diagram of a therapy system according to the invention is shown in FIG. 1. The system includes one or more remote computers 10. Each of the remote computers has a processor 12 and a memory unit 14. The computers are networked, or capable of being networked, to a server 16. A reception computer 20 can be provided to assist in the checking in of patients and the entry of new patient data fields. The reception computer has a processor 22 and a memory 26. A printer 24 and data transfer devices such as the modem 28 and fax machine 30 can also be provided.

The remote computers 10 can be either fixed station computers or portable, hand-held computers which are capable of being connected to the server by known technology. The printer 24, modem 28 and fax 30 can be selected from any suitable device. The reception computer 20 is preferably a fixed station computer, which can have a dedicated printer 32. The server 16 can be selected from suitable computer servers connected by known Local Area Networking technology.

The system of the invention can utilize currently available hardware. The invention can also be used with PEN based computers with suitable operating system software. The facsimile machine and printer can be of any suitable design. The server can be of any suitable design, and can be either a dedicated computer or one of the reception or remote computers. The hardware requirements will differ depending upon the operating system software environment. In a Windows (a trademark of Microsoft Corporation Redmond, Wash.) environment, the computer must have at least a central processor with equivalent power as the 80486 33Mhz (manufactured by Intel Corporation of Santa Clara, Calif.), and at least a 8MB random access memory and a 200MB hard disk drive. A VGA or equivalent monitor is also required.

Figure 2:
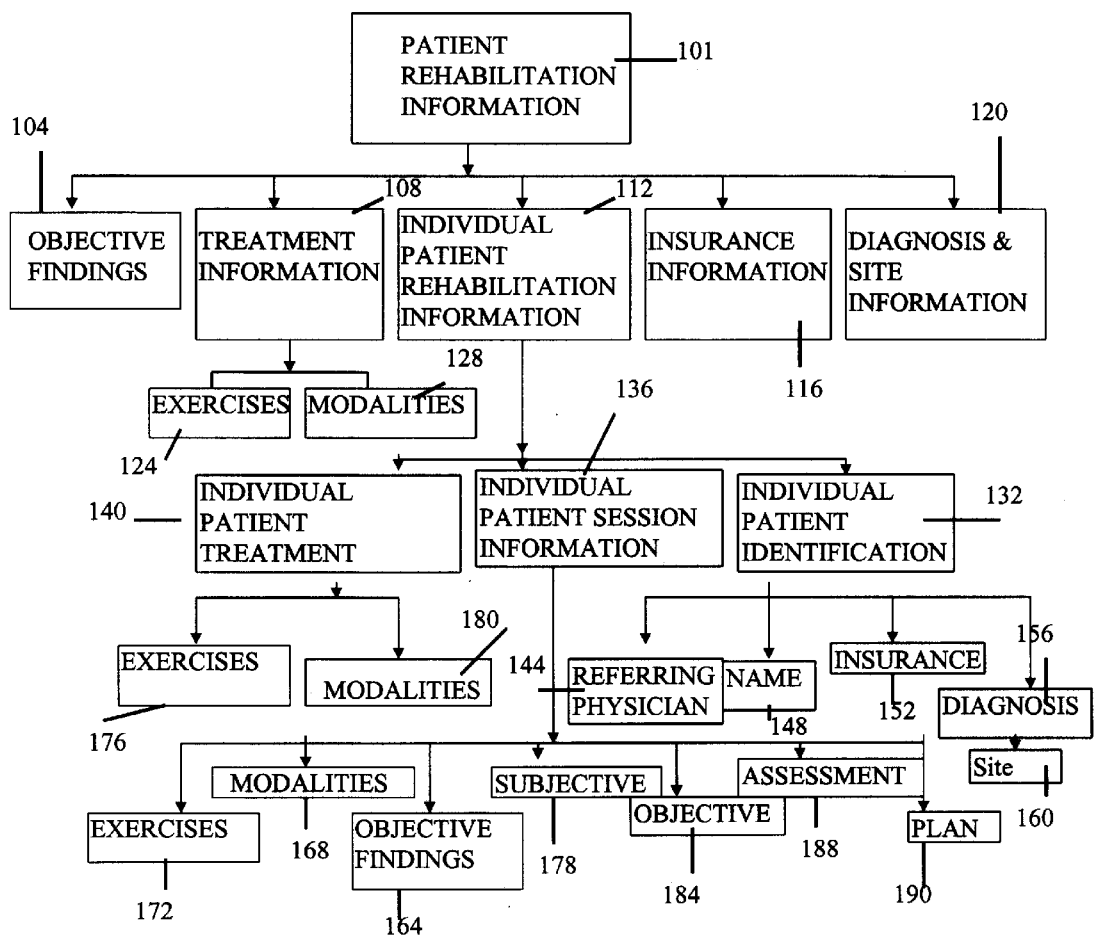
FIG. 2 is a block diagram illustrating patient rehabilitation data.

The patient rehabilitation data that is preferably utilized in physical therapy environments is shown is illustrated by the block diagram of FIG. 2. The data as a whole is a file shown as block 101. The patient rehabilitation data includes objective findings records 104, treatment data records 108, individual patient rehabilitation data records 112, insurance data records 116, and diagnosis and site data records 120. The objective findings data records 104 comprise data fields of the possible measurements taken by the therapy provider for each patient. These measurements are defined by the provider and the therapy environment. These measurements may be numerical, text, functional, or binary in nature. The treatment data records 108 comprise data fields of the possible treatments, examples being exercises 124 and modalities 128.

Individual patient rehabilitation data records 112 comprises several data fields which together make up the individual patient record. These data fields preferably comprise the listing of possible patient identifying data 132 with patient situation characteristics, and individual patient session data 136 and individual patient treatment data 140. The individual patient identifying data can include data such as the referring physician 144, patient name 148, insurance data 152, diagnosis data 156 and site data 160. The individual patient session data 136 can include objectives finding data 164, modalities data 168, exercises data 172, subjective data 178, objective data 184, assessment data 188, and plan data 190. The individual patient treatment data 140 can include modalities data 176 and exercises data 180.

Figure 3:
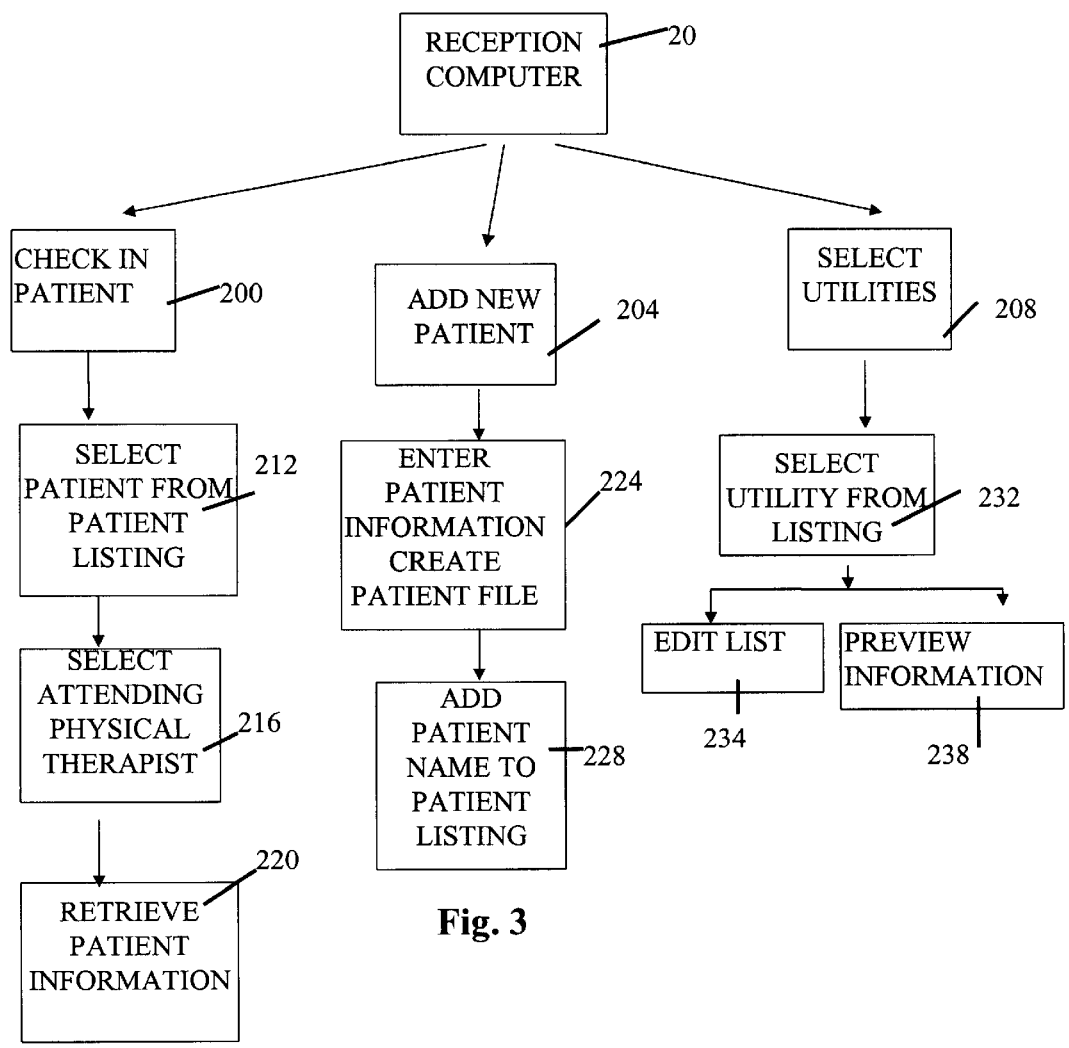
FIG. 3 is a block diagram illustrating steps according to the method of the invention as performed at a reception computer.

The reception computer 20 performs a number of functions, as illustrated in FIG. 3. These functions include checking in the patient 200, adding new patients 204 and selecting utilities 208. Checking in patients 200 includes the steps of selecting patients from patient listings 212, selecting an attending therapist 216 and retrieving patient data 220. Adding a new patient 204 includes the steps of entering patient data to create a patient record 224, and adding the patient name to the patient listing 228. Selecting utilities 208 can include the steps of selecting the desired utility from a listing 232, and editing the list 234 or previewing patient data 238.

Figure 4:
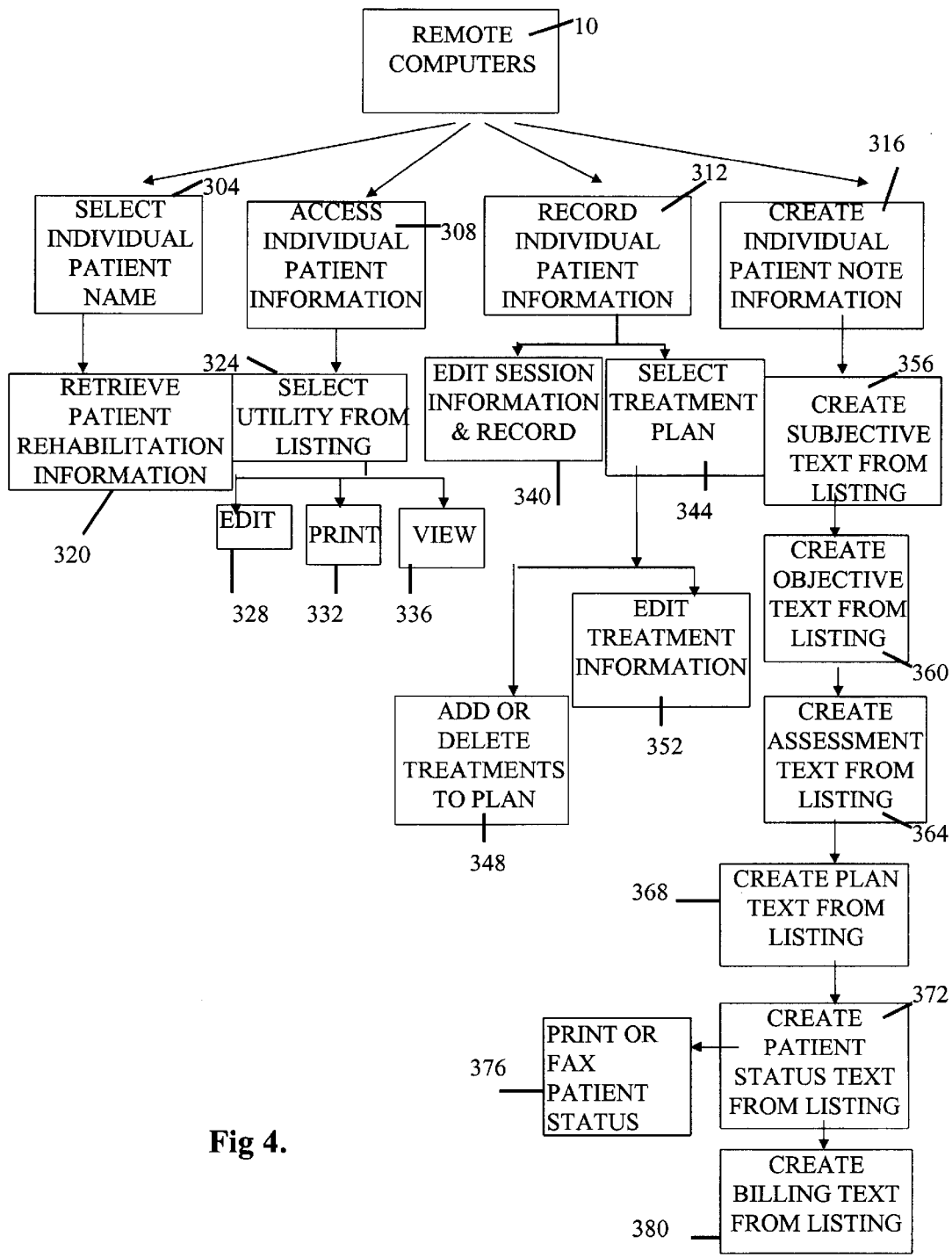
FIG. 4 is a block diagram illustrating steps according to the method of the invention as performed at a remote computer.

The remote computers 10 perform a number of functions, as illustrated in FIG. 4. These steps include selecting individual patient name 304, accessing individual patient data 308, recording individual patient data 312, and creating individual patient note data 316. The selection of individual patient name 304 includes the step of retrieving individual patient rehabilitation data 320, which is all or a portion of the overall patient record. Accessing individual patient data 308 includes selecting a utility from a listing 324 and is used to edit 328, print 332, or view 336, the individual patient data.

Recording individual patient data 312 includes the steps of editing and recording session data 340, and selecting a treatment plan 344. Selecting the treatment plan 344 can include the steps of adding or deleting treatments to the plan 348, and editing treatment data 352.

Figure 5:
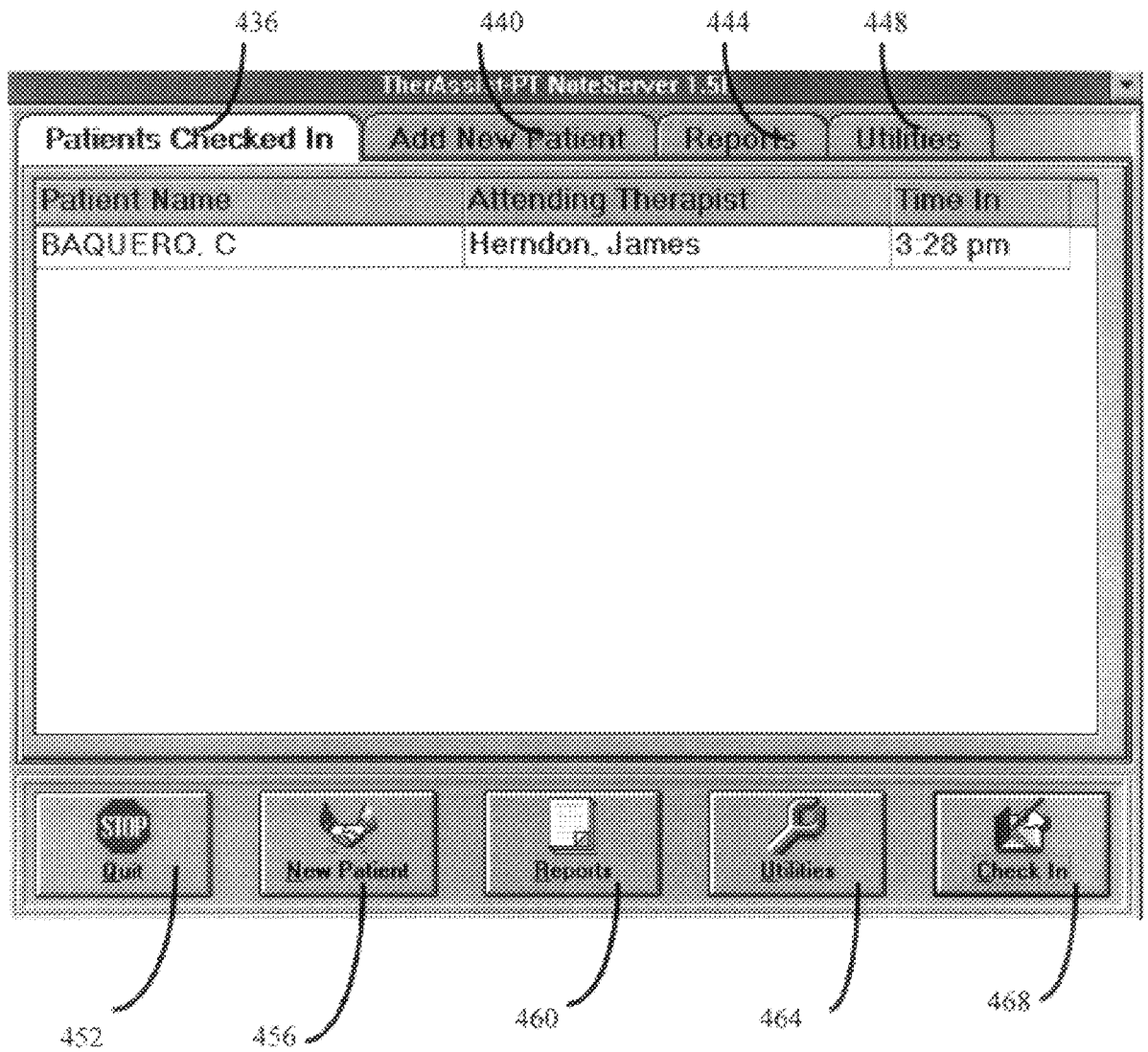
FIG. 5 is a screen for a reception computer used to determine which patients are present for therapy.

The system can be used to create an individual patient note 316. This can include the steps of creating subjective text from a listing 356, creating objective text from a listing 360, creating assessment text from a listing 364, creating plan text from a listing 368, and creating patient status text from a listing 372. The patient status can be printed or sent 376 using a modem, local area network, facsimile local printer, or the like. A billing text can also be created from a list 380. The above blocks of FIGS. 3–4 each represent a series of program instructions that are executed depending upon the therapy provider's use of the programmable computer. Each visual object on the screen, such as the tab 440 in FIG. 5, represents one or more sets of program instructions. The blocks of program instructions will retrieve and utilize data fields from memory. Blocks that include data input the therapy provider or receptionist will also incorporate data input devices such as alpha numeric keyboards, touch screens, and the like. Data inputs will be stored in memory by means known in the art. The flow, display and manipulation of the data, as well as the control of program steps, is performed by the central processor of the reception computer 20 or remote computers 10. Manipulation of data at the remote computer is performed by the processor at said computer.

The software for the invention is preferably of the graphical interface "MS Windows" a product of Microsoft Corporation of Redmond, Wash. The main screen of the reception computer 20 is shown in FIG. 5. This screen has a tab 436 for checking in patients, a tab 440 for adding patients, a tab 444 for seeing the reports of patients and a tab 448 for modifying data. A button 452 stops the program. A button 456 is provided to enter data for a new patient. A reports button 460 generates reports. A utilities button 464 is provided to initiate programming which will modify the data in the program. A check in button 468 is provided to initiate programming which will check in patients.

Figure 6:
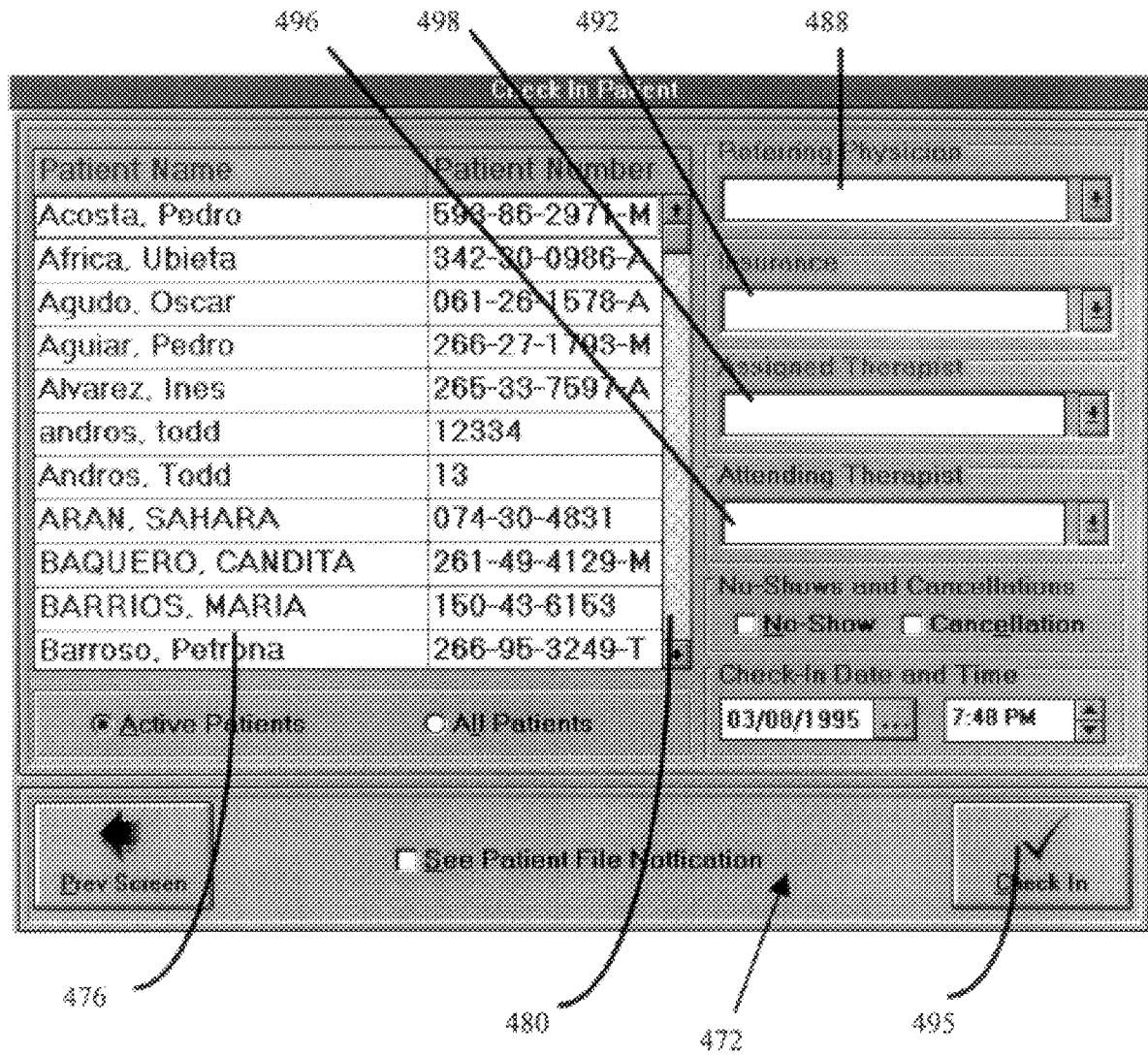
FIG. 6 is a screen for a reception computer used during the check-in process.

The arrival of a patient requires the reception operator to push the patient check in tab 436 or button 468. A check in screen 472 shown in FIG. 6 will appear. A list of patients 476 will be presented. The operator can scroll using button 480, or other suitable input device, to arrive at the name of the patient. Upon selecting a patient name a list of therapists assigned to, or suitable for, that patient will appear. Upon selecting the name of an appropriate therapist, the selected name will appear in the attending therapist box 496. Other spaces are used to select the referring physician 488, the insurance carrier 492, and the attending therapist 496 when a patient returns for therapy after the completion of previous therapy. To complete the check-in process the operator presses the check-in button 495.

Figure 7:
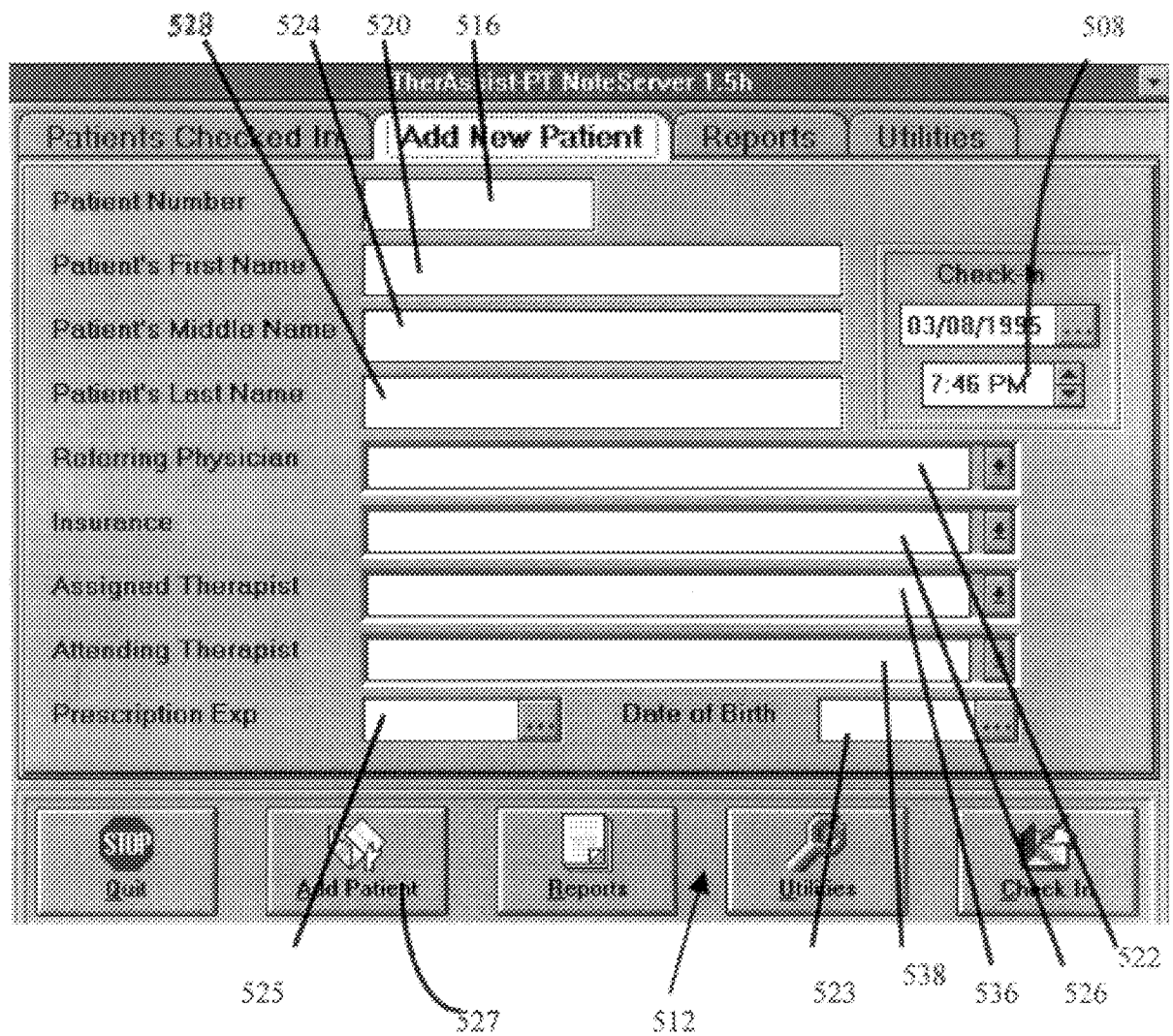
FIG. 7 is a screen used to add new patients.

If the patient has not been seen at the clinic before, data will have to be entered into the system for the patient. New patient data can be added by pressing the add new patient tab 440 or the new patient button 456 (FIG. 5). The screen 512 shown in FIG. 7 will appear for entering data concerning the patient. The patient number will be entered 516, a first name 520, a middle name 524, a last name 528, date of birth 523, and prescription expiration 525. A referring physician 522 will be entered along with an assigned therapist 536, an attending therapist 538, and insurance type 526. The add patient button 527 is pressed when data has been entered.

Figure 8:
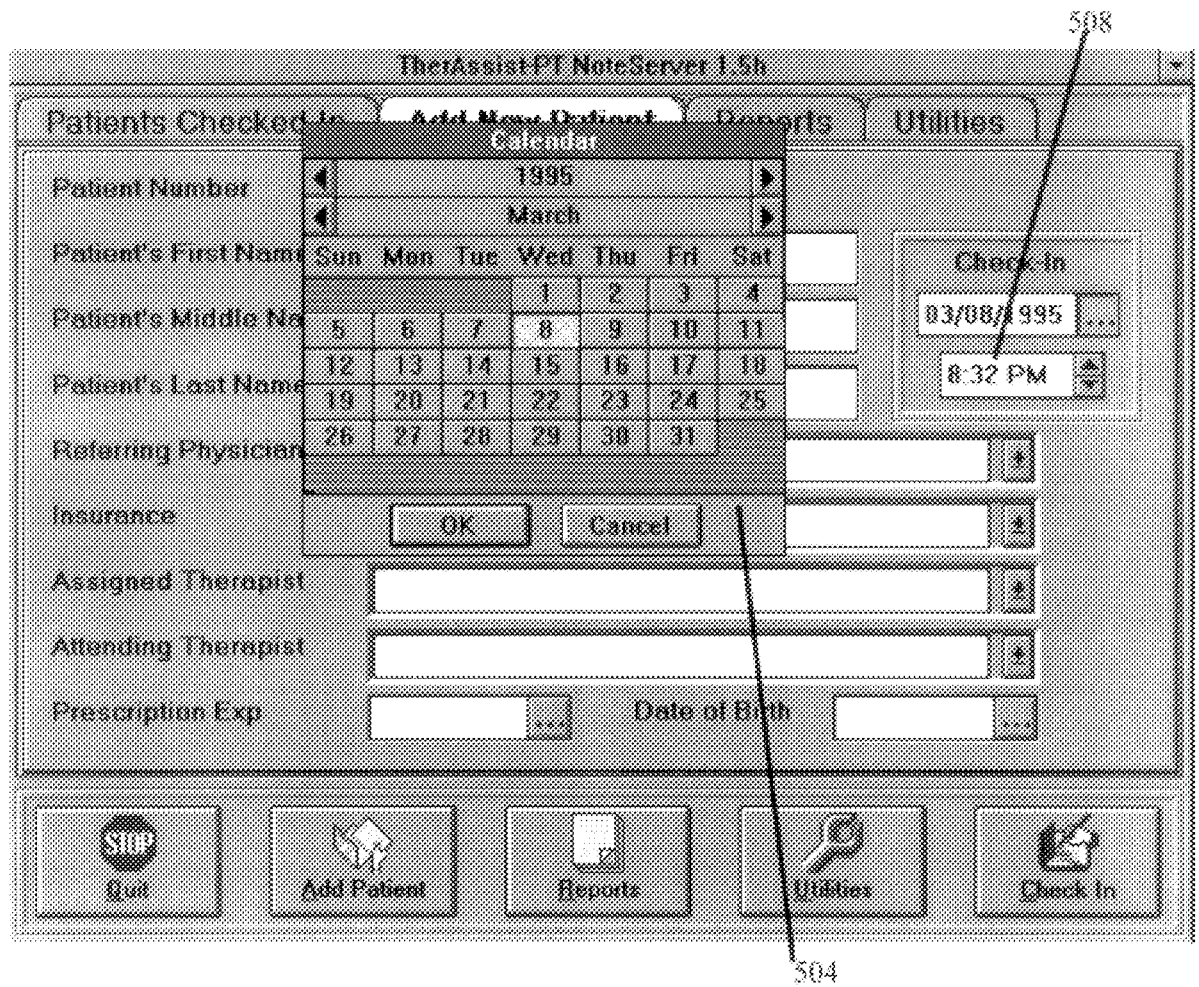
FIG. 8 is a screen for a reception computer used to change dates.

The date can be modified using an on-screen calendar shown in FIG. 8. The calendar 504 appears on the screen and appropriate entry can be made as to year, month, and date to enter the appropriate date. The time can be altered using an on-screen timer 508.

After the patient has been checked in, and any new patient data has been entered, the assigned therapist will be signaled that the patient has arrived. The remote computer has a screen shown in FIG. 9. This screen displays patient names through tabs 564. Buttons are provided such as the stop button 568, utilities button 572, the patient work button 576, and the SOAP notes button 580.

Figure 10:
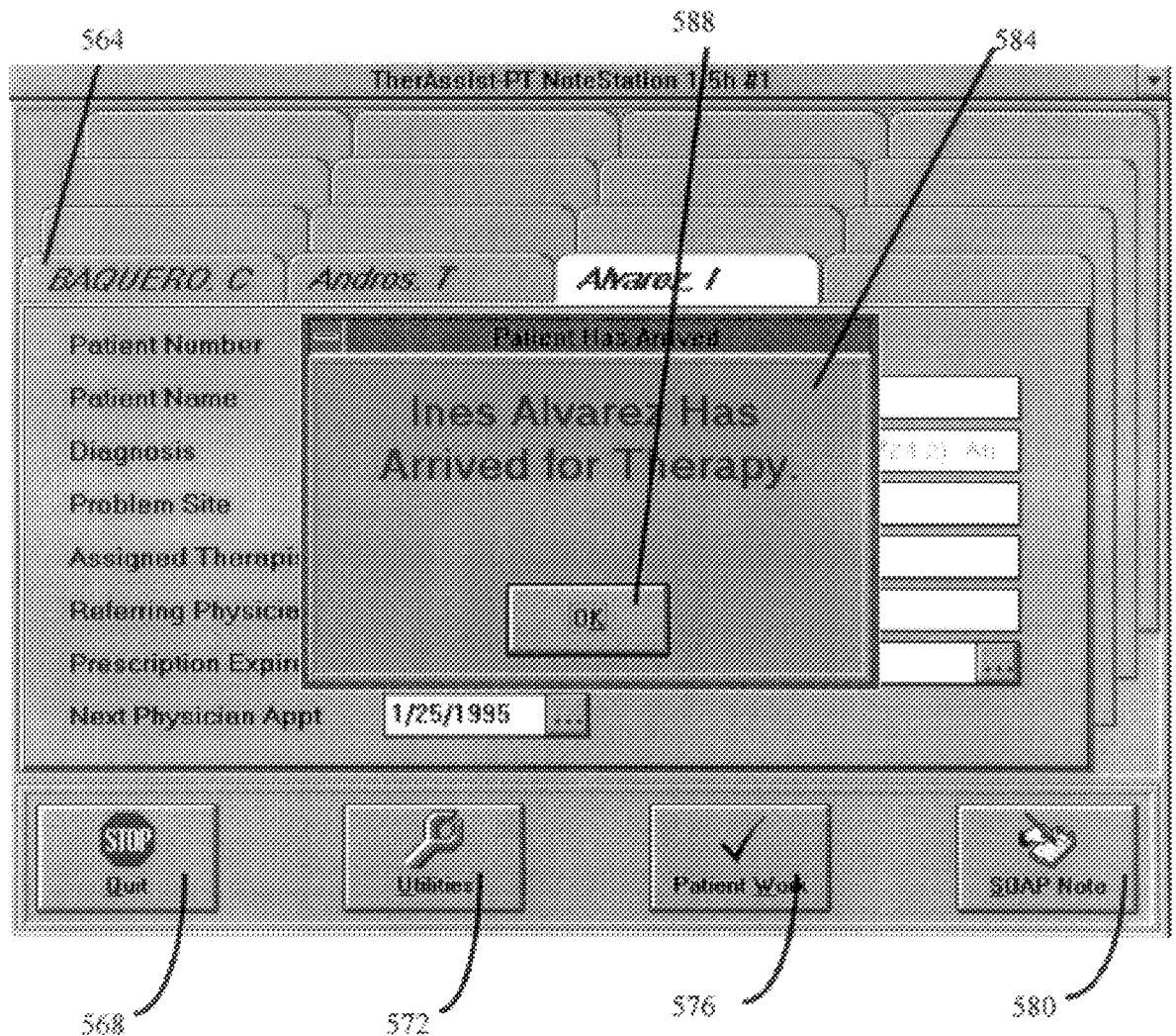
FIG. 10 is a screen used to notify a therapist that a patient has arrived for therapy.

Upon the arrival of a patient a signal is transferred from the reception computer 20 through the server 16 to the particular remote computer 10 of the assigned therapy provider, as shown in FIG. 10. A signal window 584 appears to indicate that the patient has arrived. The window can be removed by pressing the OK button 588. The file for the respective patient will automatically be sent by the server 16 to the appropriate remote computer 10 of the assigned therapy provider.

Upon the arrival of the patient, a flow sheet (FIG. 11) will preferably be printed, as by the printer 24. The flow sheet is a document which allows the therapist to conveniently have at ready disposal a list of the treatments which the patient is to receive at the therapy session. The flow sheet also preferably records the results of previous sessions with the patient, so that the therapy provider can readily ascertain the progress and current status of the patient. Other data such as referring physician, problem site, diagnosis, insurance, date of birth, initial visits and total visits can also be provided. The goals of the therapy are also preferably indicated. Each exercise and modality can be modified to have individual patient notes, and be reordered to indicate the order in which therapy treatments are to be provided.

The therapy provider then performs the therapy session with the patient. Data as to patient performance and status can be written down to be entered at a later time or, if the remote computer 10 is hand held, the data can be entered throughout the therapy session. The patient work button 576 (FIG. 9) is pressed to display the screen 592 for the therapy session, as shown in FIG. 12. The screen includes a column 596 for providing a description of the different treatments. Other columns can provide indications of whether the treatment is "on hold" 598, or not to be provided. The set number 600, the number of repetitions 602, the weight 606, the duration 610 and an indication of whether the treatment was completed 614, can be provided in additional columns. The therapist enters an indication for each item that was performed, or an indication that the therapy was not performed.

Data can be entered into the computer in a variety of ways. The data that has only a yes/no alternative, such as the "on hold" 598 or "completed" 614 columns, the computer can toggle between "yes" and "no" answers at the selection of the therapy provider. The selection can be made by pen, mouse, manual entry, or by touch screen computer. Data with a variety of alternatives will be presented sequentially, with a different alternative appearing upon each selection by the therapy provider, the therapy provider touching the screen until the appropriate entry appears.

Figure 13:
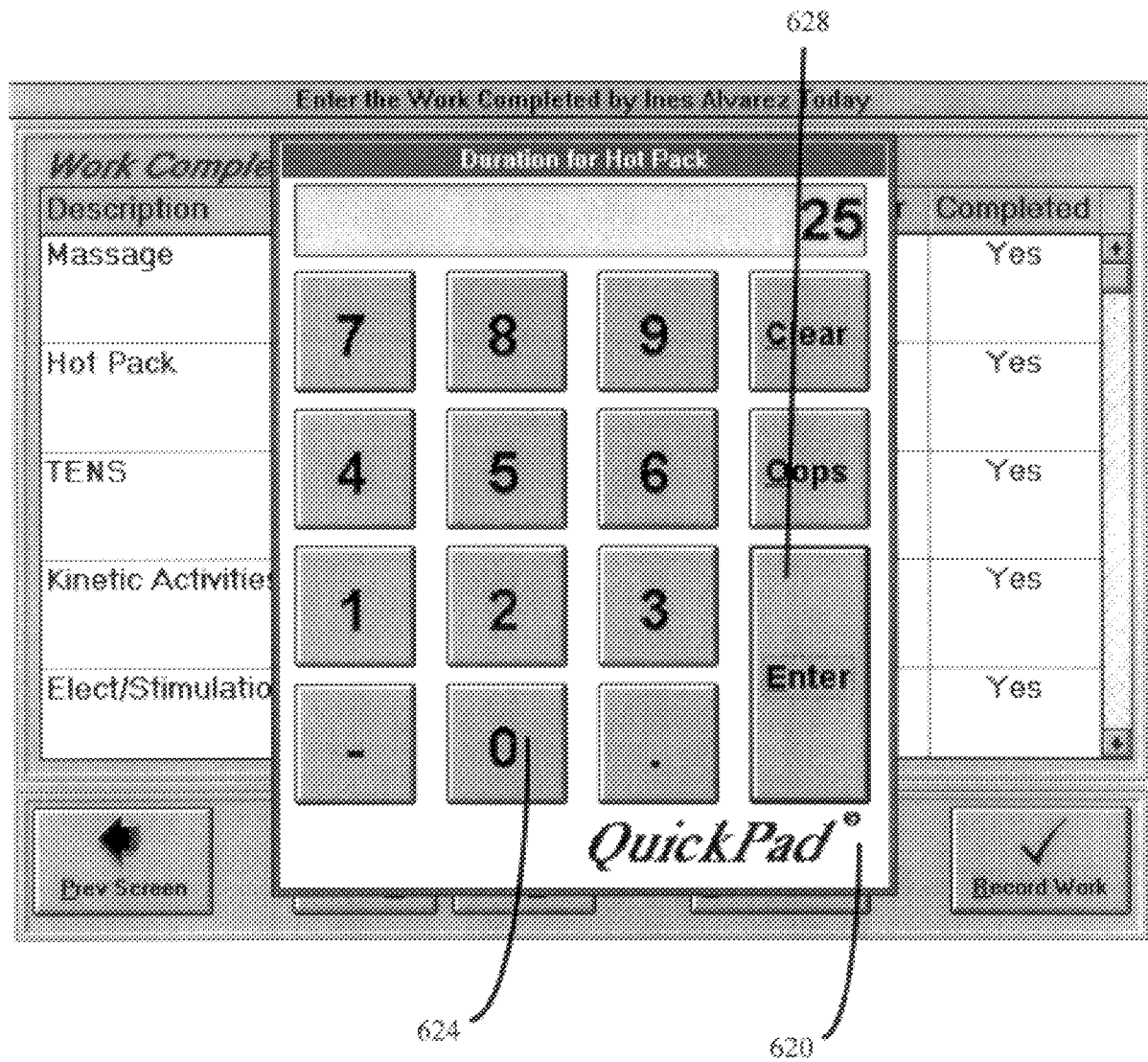
FIG. 13 is a screen showing the entry of numerical data using an on-screen key pad.

Numerical data is preferably entered by a key pad, which preferably is an on-screen key pad as shown in FIG. 13. The key pad 620 preferably appears each time the therapy provider indicates by touching or otherwise entering a data field which requires a numerical entry, such as the sets 600, reps 602, weight 606 or duration 610 columns. The numerical data can be entered by touching the keys 624, and then pressing the enter key 628. Suitable software for on-screen keypads is available from vendors. The keypad 620 will disappear when the enter key 628 is pressed, and the entered number will appear in the appropriate column.

The therapy provider must produce a report upon completion of the therapy session, to record the results of the session for the patient file, for any physician or supervising authority, for purposes of modifying the treatment, and for billing. The Record Work button 632 is pressed to record all of the data that has been entered during the therapy session. The main screen 560 will appear again. The SOAP Note button 580 is pressed to make file entries for the individual patient. The SOAP Note is used in therapy as a mnemonic for "Subjective", "Objective", "Assessment", and "Plan". These are areas of data which must be recorded or made by the therapy provider according to professional standards to properly record the results of the session and the status of the patient.

Figure 14A:
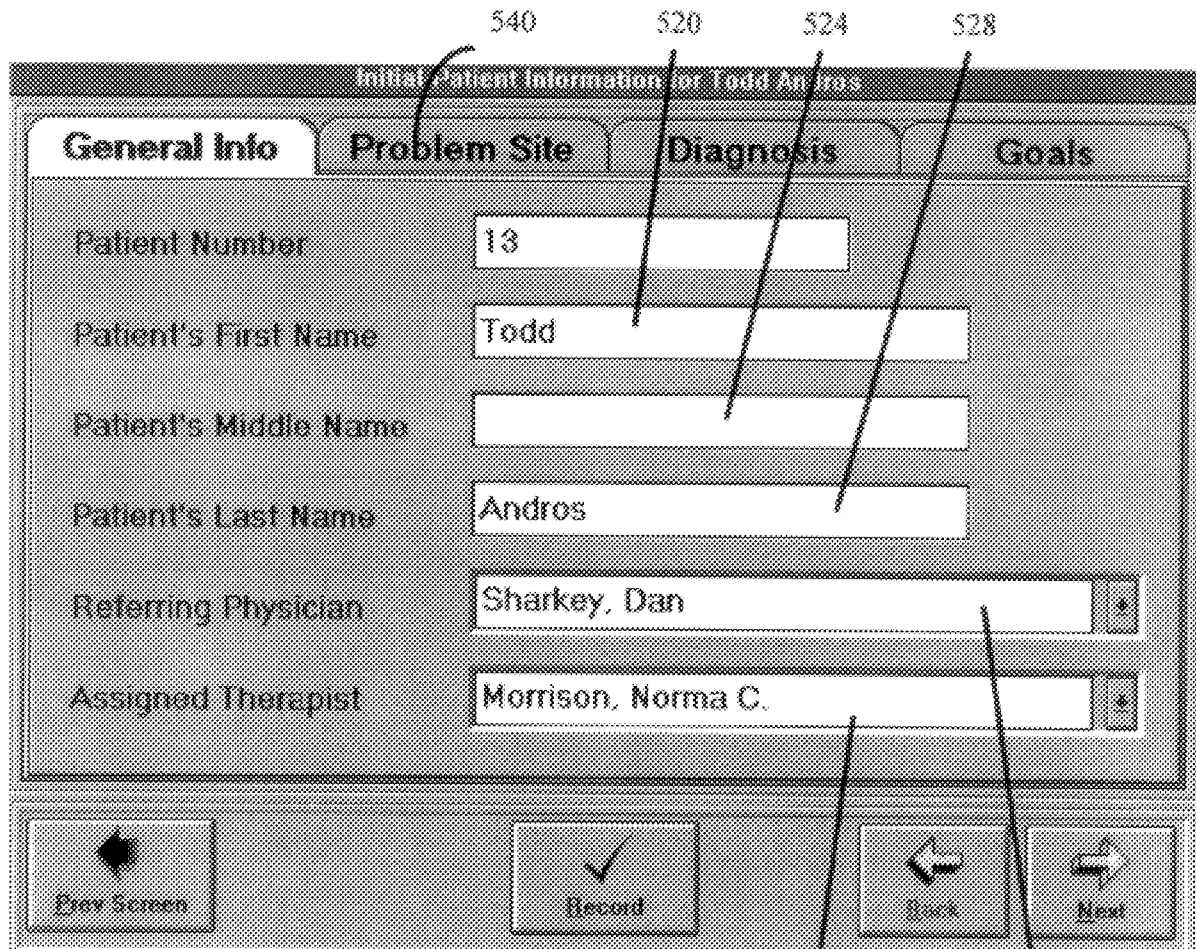
FIGS. 14a–e are progressive screens used to enter initial patient data such as patient problem site, diagnosis, and goals.
Figure 14B:
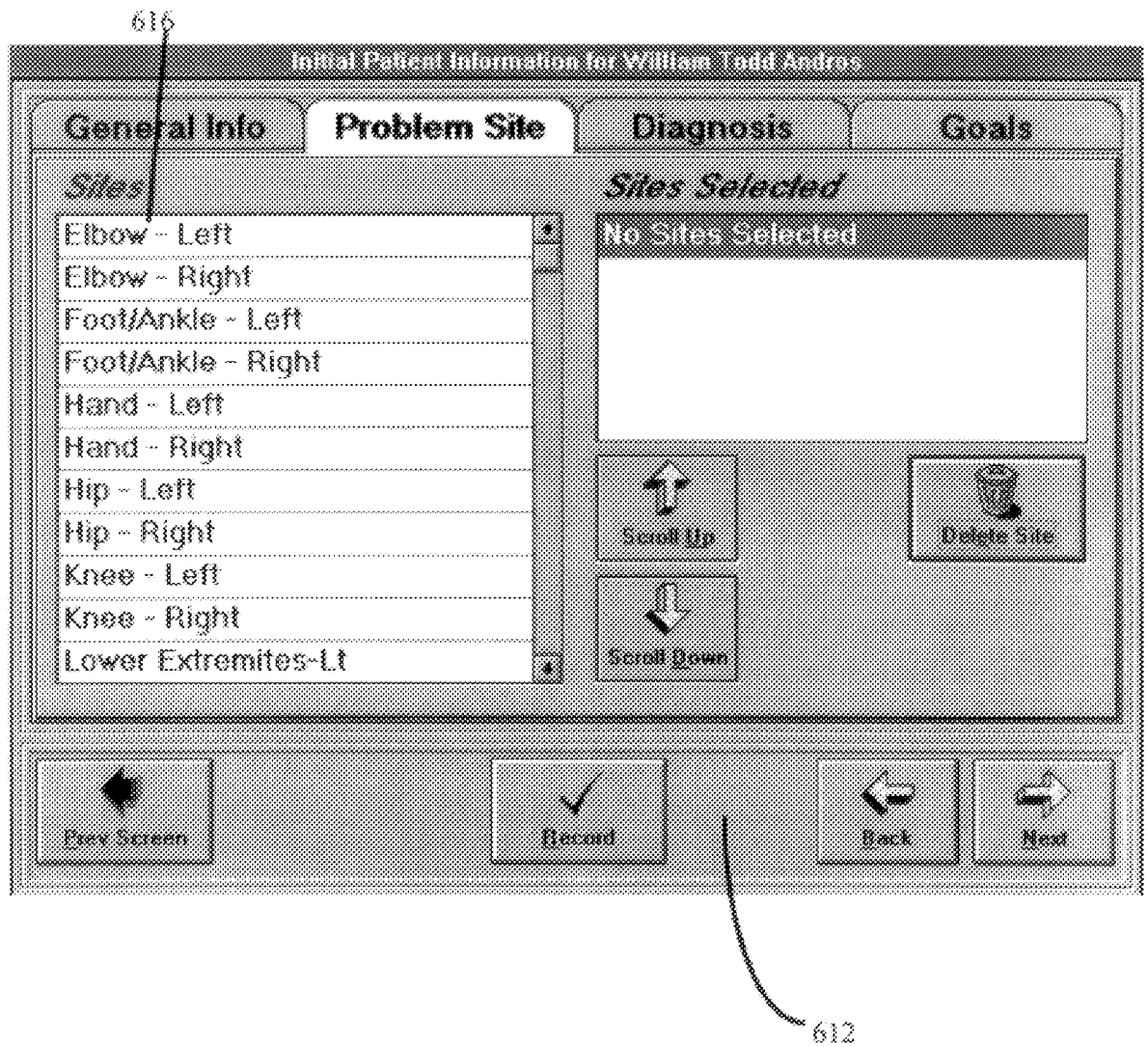
Figure 14C:
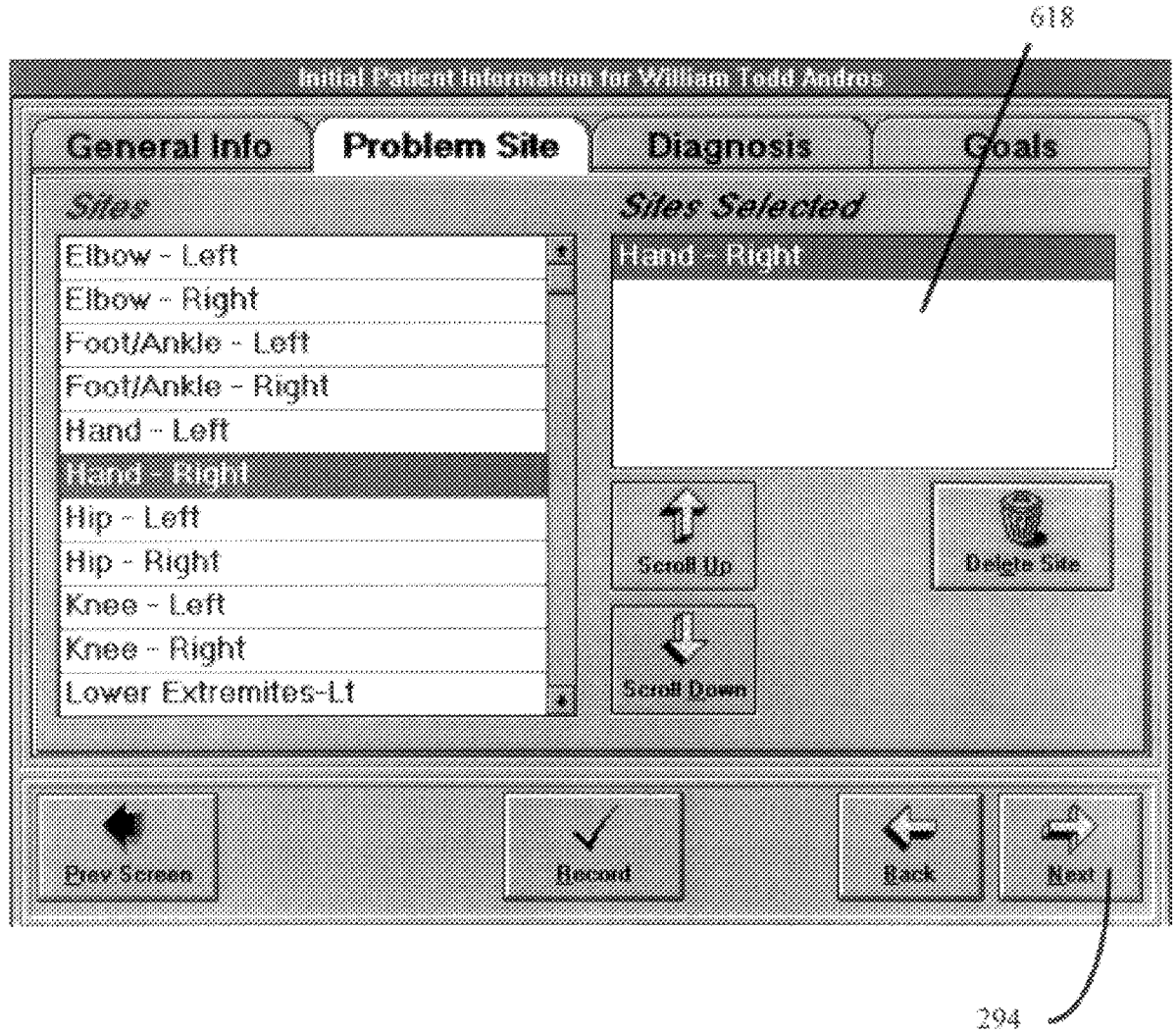
Figure 14D:
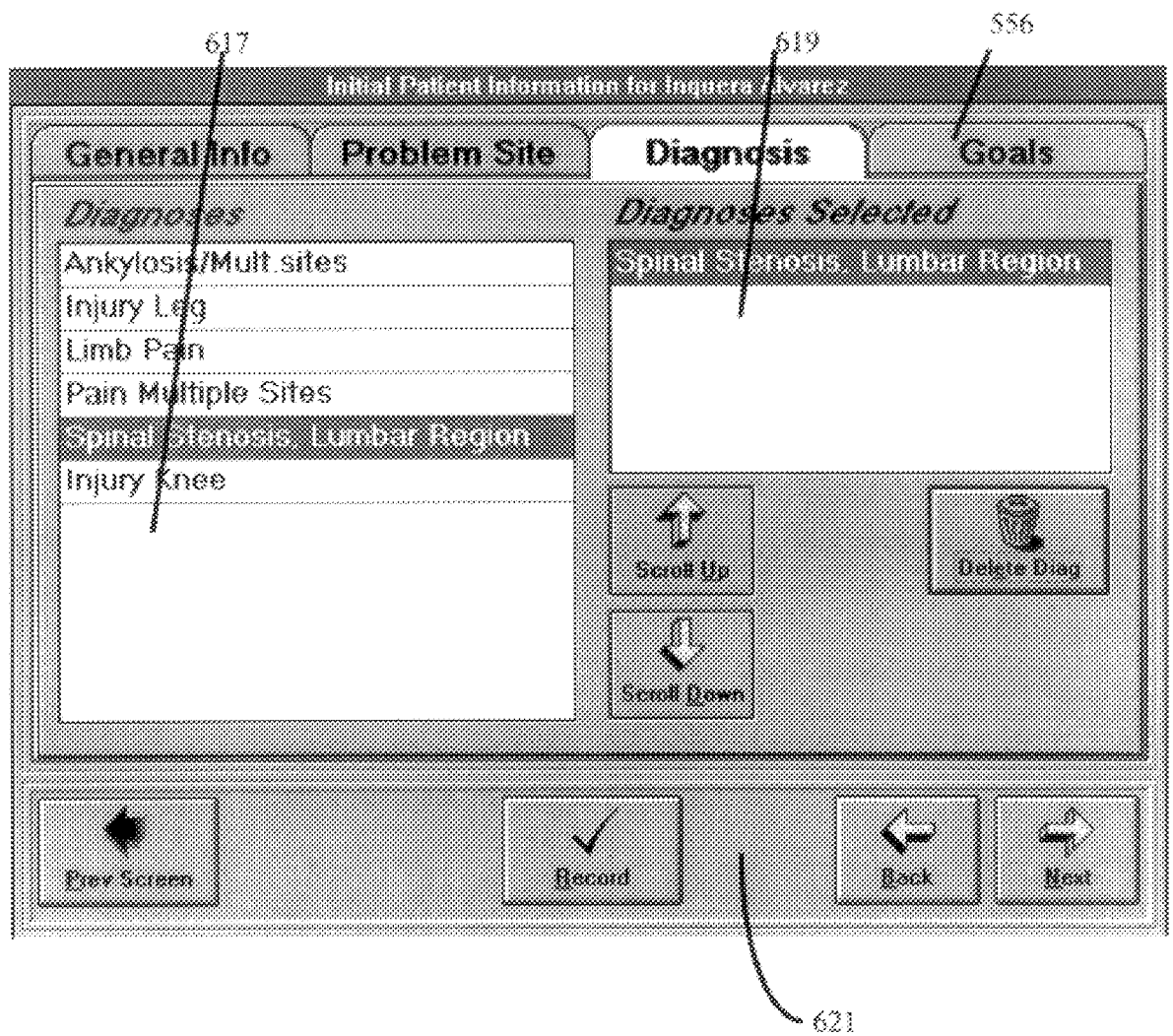
Figure 14E:
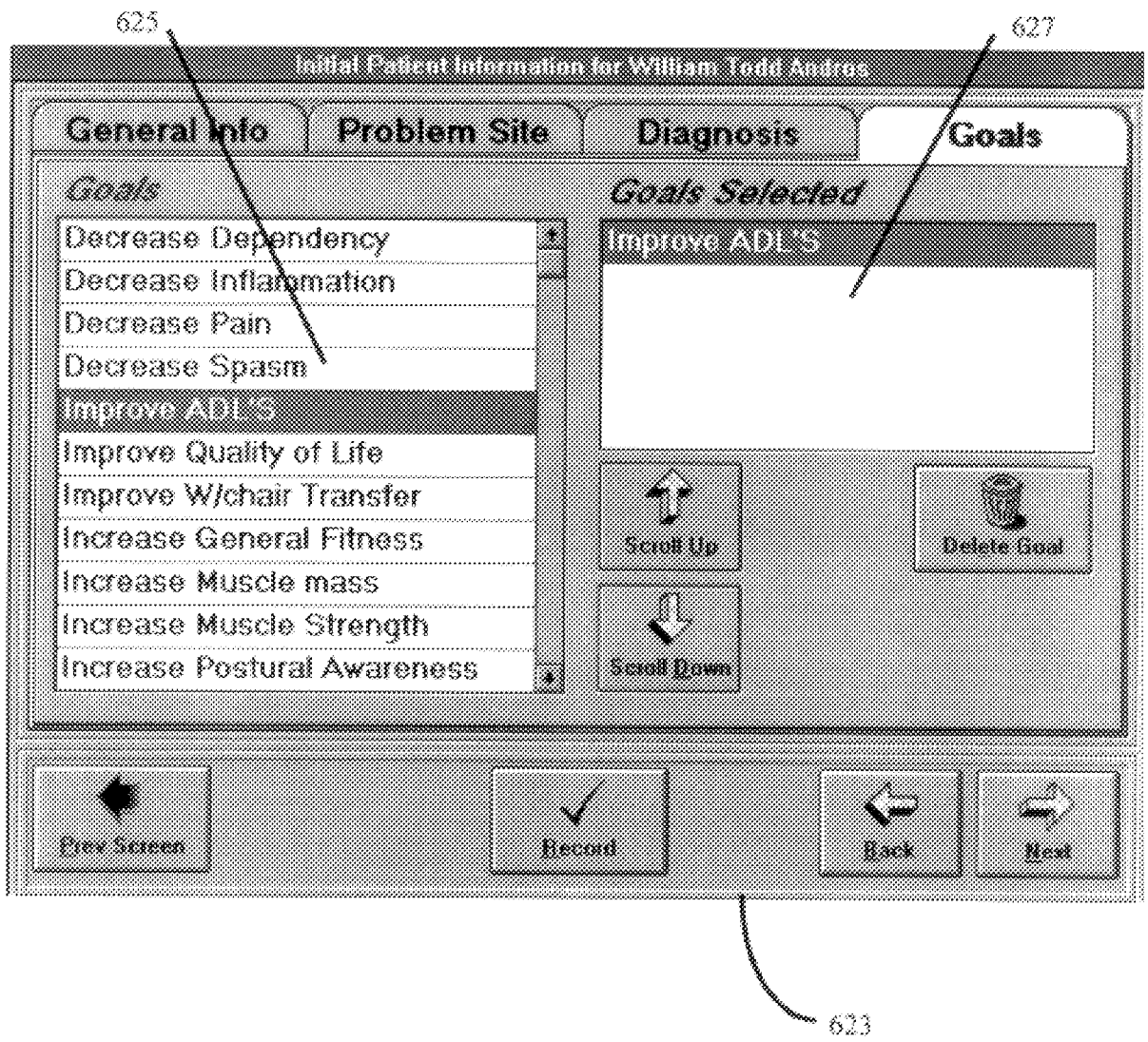

The therapist must enter initial patient data when creating a SOAP note for the first visit. This is accomplished when pressing the SOAP button 180 shown FIG. 9. The screen shown in FIG. 14*a* will appear. The patient identifying data such as patient first name 520, middle name 524, last name 528, referring physician 522, and assigned therapist 536 will appear. This data will usually have already been entered at the reception computer 20, but can be entered by the therapy provider on screen (FIG. 14*a*) with an alphanumeric input device. Pressing the problem site tab 540 will cause the display of the screen 612 (FIG. 14*b*), which allows for the entry of individual problem data, principally the locations of the areas to be treated. A list of possible sites appears in area 616. Site selected from the list in area 616 will appear in a sites selected area 618 (FIG. 14*c*). The diagnosis tab 548 or the next button 294 are pressed when the selection of sites has been completed. The diagnosis screen shown in (FIG. 14*d*) will appear. A list of possible diagnosis will appear in area 617. Diagnosis selected from the list in area 617 will appear in the diagnoses selected area 619 (FIG. 14*d*). The goals tab 556 or the next button 294 are pressed when the selection of diagnosis are completed. The goals screen 623 shown in (FIG. 14e) will appear. A list of possible goals will appear in area 625. Goals selected from the list in area 625 will appear in the goals selected area 627. The next button 294 is pressed when the desired goals have been selected. The therapy provider must then enter SOAP findings for the particular therapy session. The invention assists the therapy provider in creating SOAP records.

The computer stores predefined, context sensitive phrases with which the therapy provider can build sentences automatically upon the selection of data fields from the lists. Selection of items from the list stores these fields into memory. The predefined phrases associated with each type of data are retrieved and stored by the computer to build a sentence as the data is entered.

The lists of data fields can be displayed individually or, upon pressing a button, displayed in tandem to assist in the rapid construction of a sentence from multiple tables of data fields. Selected records of patient rehabilitation data are provided as lists of data fields. The listed data fields can be modified according to the preference of the therapy provider or the needs of the patients. These records, and the various options and alternatives that make up the individual data fields for each record, are stored in memory. Visual representations of the patient rehabilitation data, such as abbreviations or symbols, can be displayed in place of the complete text. The process of constructing text from tables of patient rehabilitation data fields is shown in FIGS. 15–16.

Figure 9:
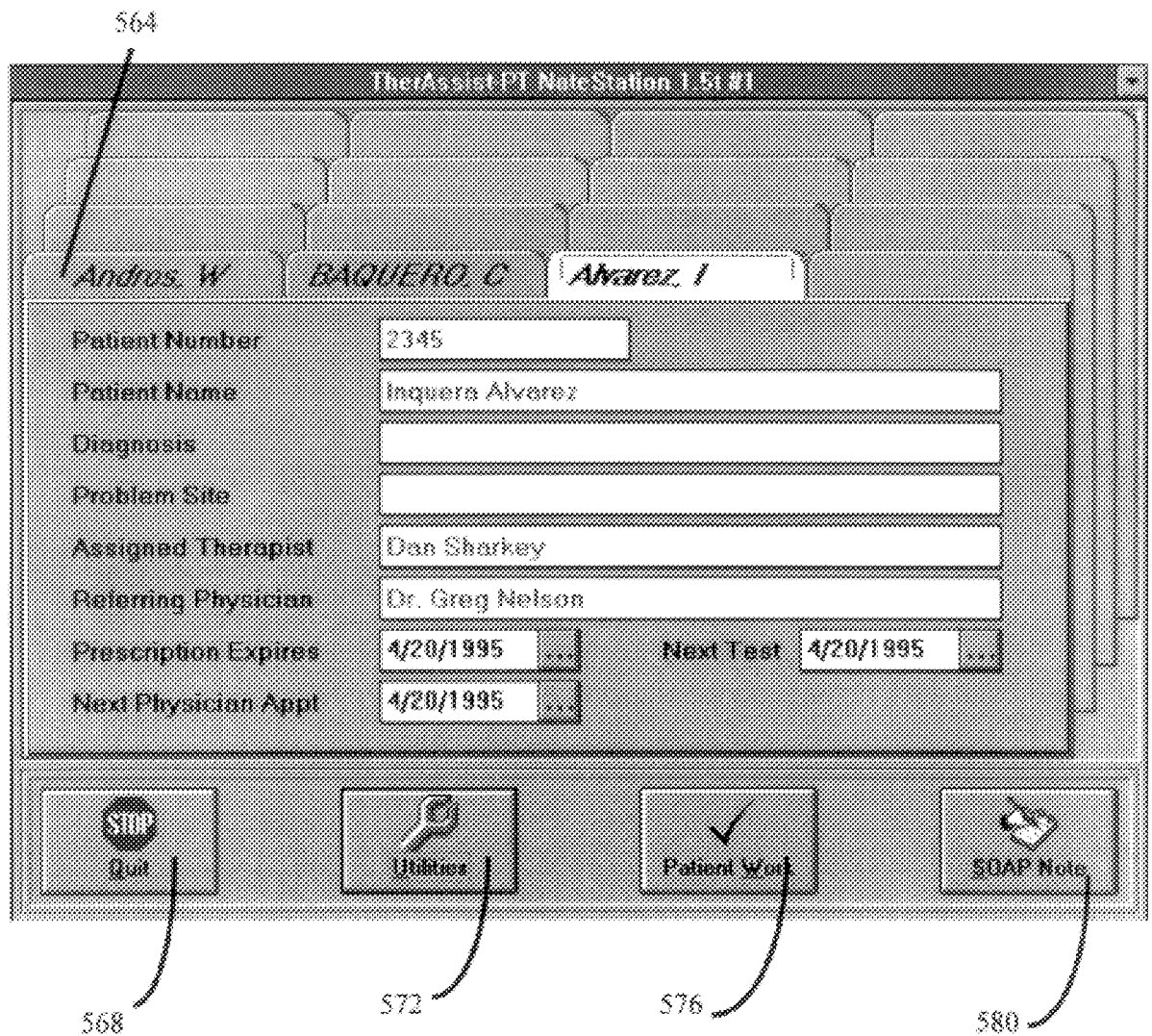
FIG. 9 is a screen used for a remote computer to display all patients that are present for therapy.
Figure 15A:
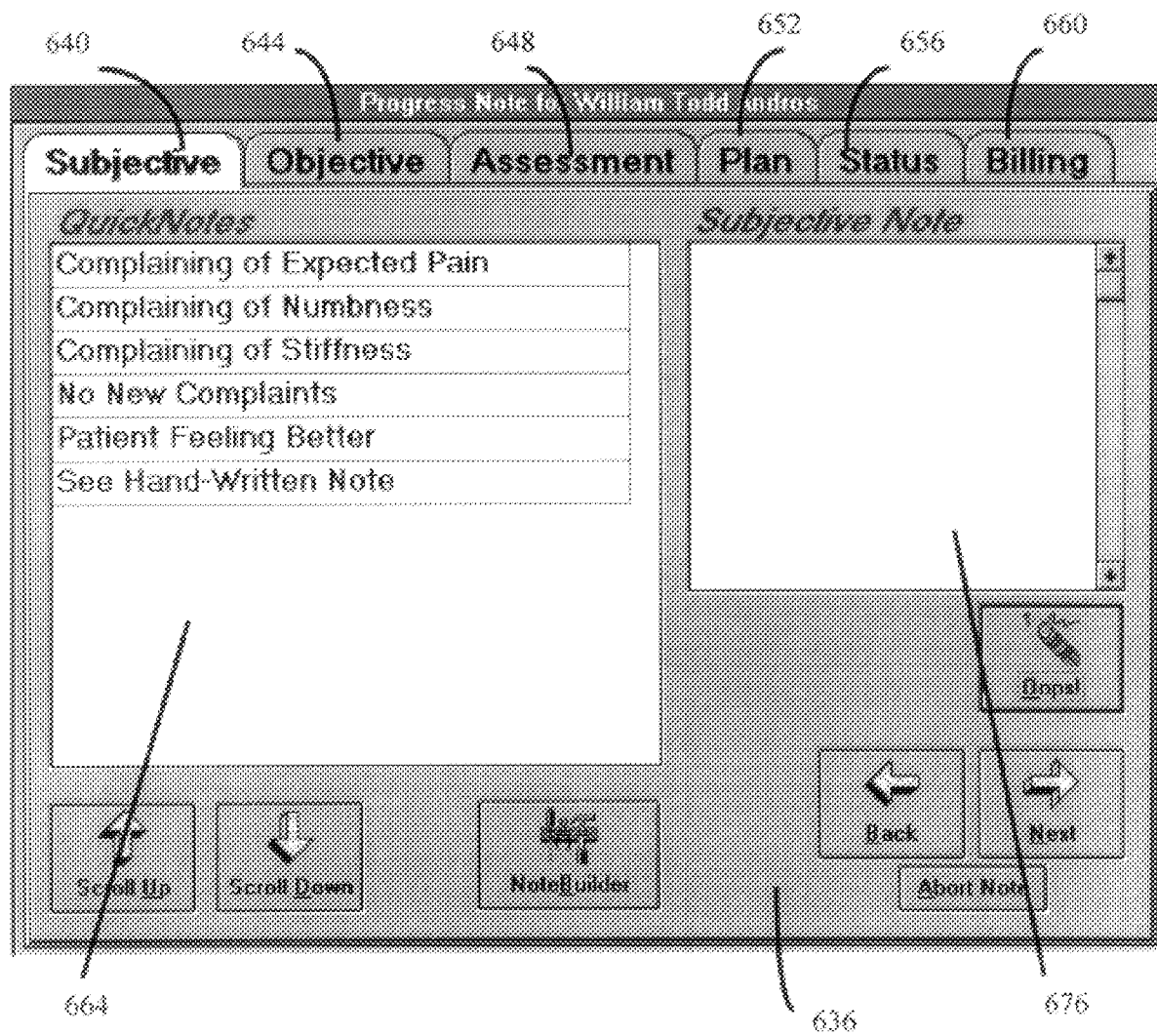
FIGS. 15a–c are progressive screens showing the construction of subjective notes.

The subjective notes screen 636 shown in FIGS. 15 a–c will appear after initial SOAP data is entered as described above or, for an existing patient, upon pressing the SOAP Note button 580 (FIG. 9). The subjective screen 636 preferably appears initially, as this is the first entry that is typically made by therapy providers. The subjective tab 640 will be highlighted. Other tabs are provided for the entry of objective 644, assessment 648, plan 652, status 656 and billing 660 data from the therapy session. The therapy provider must then enter subjective findings concerning the patient, such as patient complaints, symptoms and the like. An area 664 is preferably provided in which common complaints are listed. The therapy provider can scroll through the list using the scroll tab 480. The particular listing will be entered upon touching the screen at the list which automatically enters each of the complaints of the patient. Upon entering a particular complaint, the selected complaint will appear in the area 676.

Figure 15B:
Figure 15C:
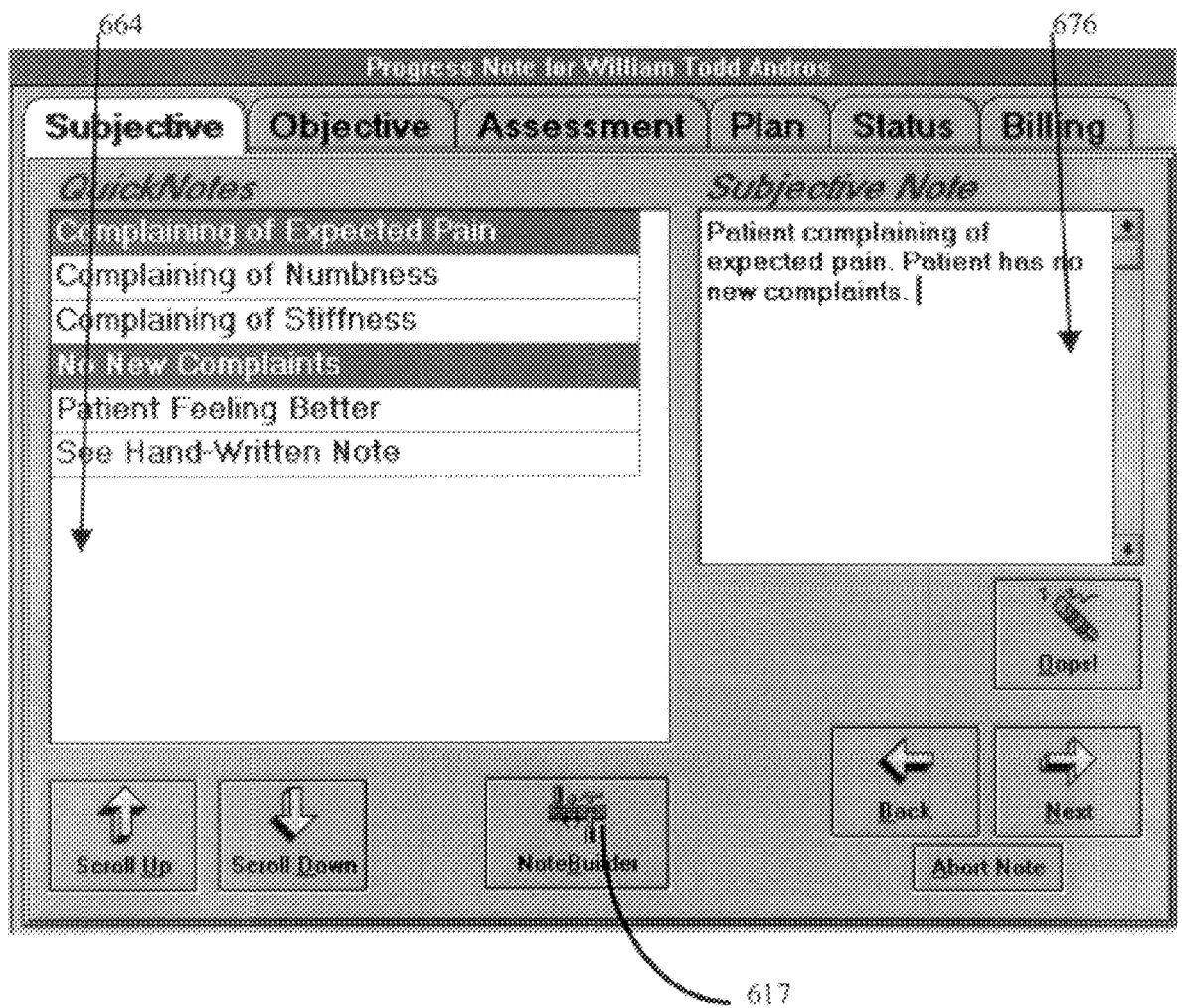

The selection of "Complaining of Expected Pain" in FIG. 15b automatically appears in the Subjective Notes area 676 as "Patient complaining of expected pain". Similarly, selecting the phrase "No New Complaints" in FIG. 15b results in the completion of the sentence "Patient has no new complaints", which appears in the are 676 shown in FIG. 15c. Another list will indicate the location, such as "inferior", and "right". The Note Builder™ button 617 is pressed for this function.

Accordingly, a complete text description of this patient rehabilitation data can be created merely by selecting the appropriate entries in the table area 664.

Figure 16A:
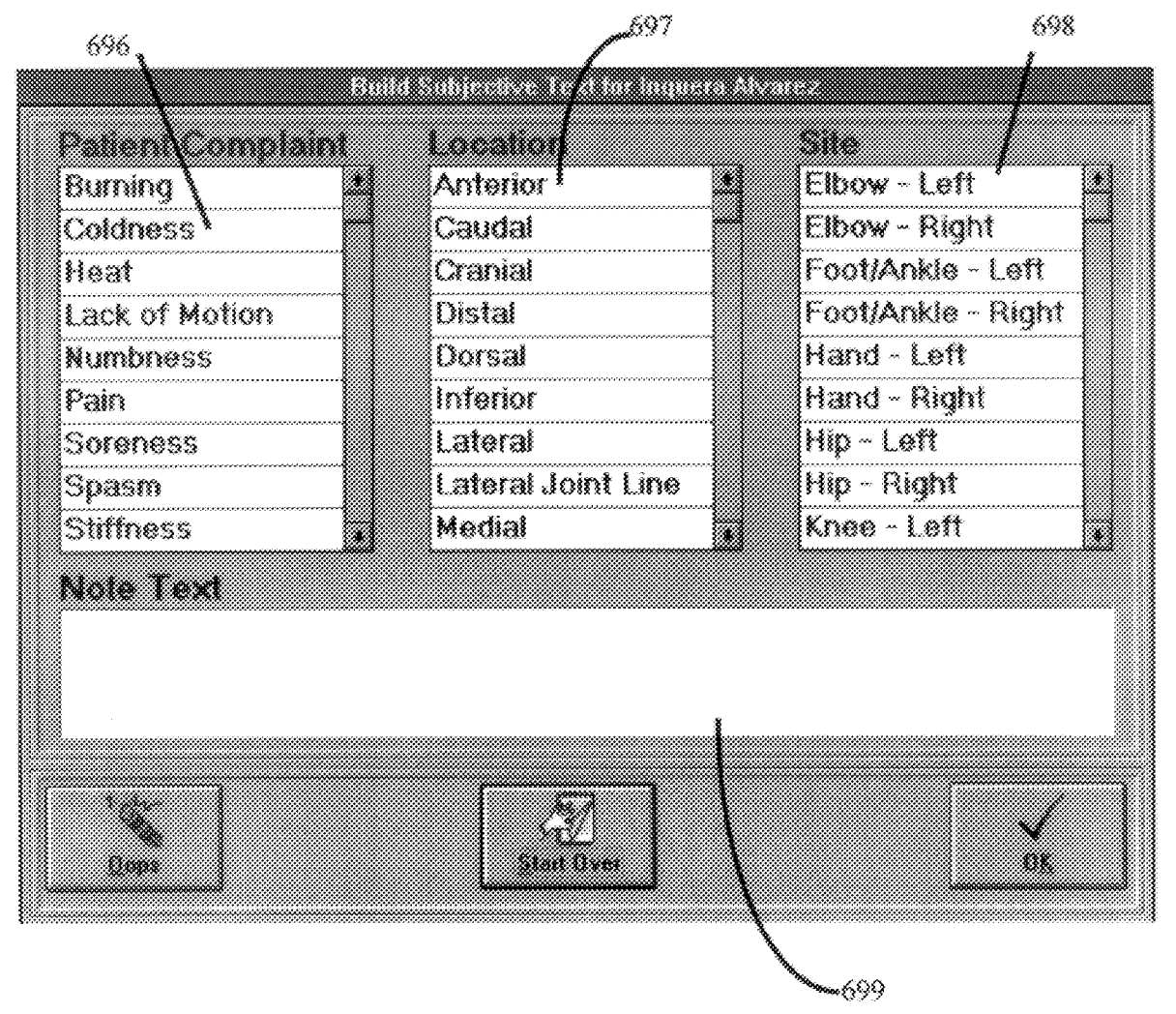
Figure 16C:
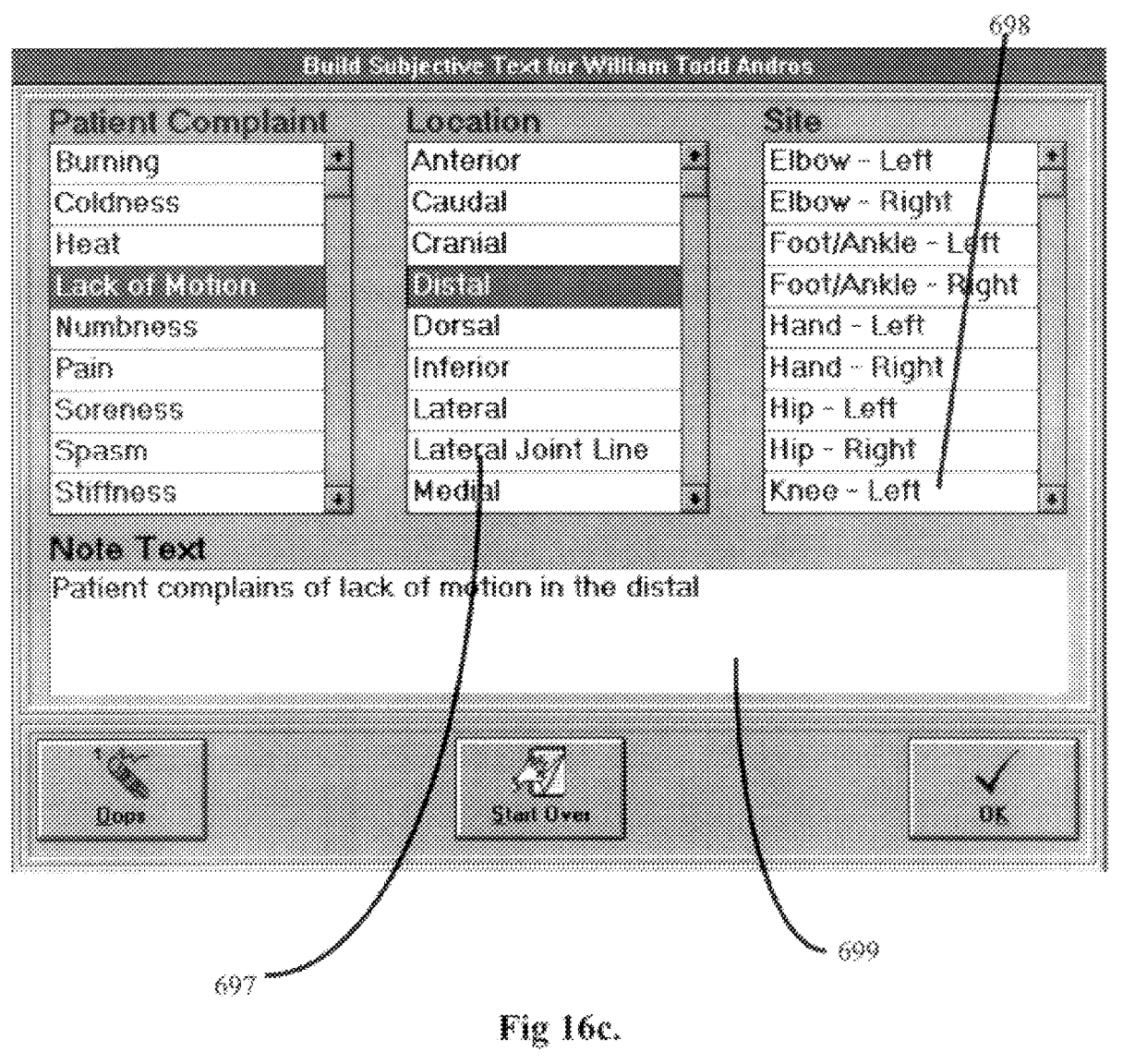
Figure 16D:
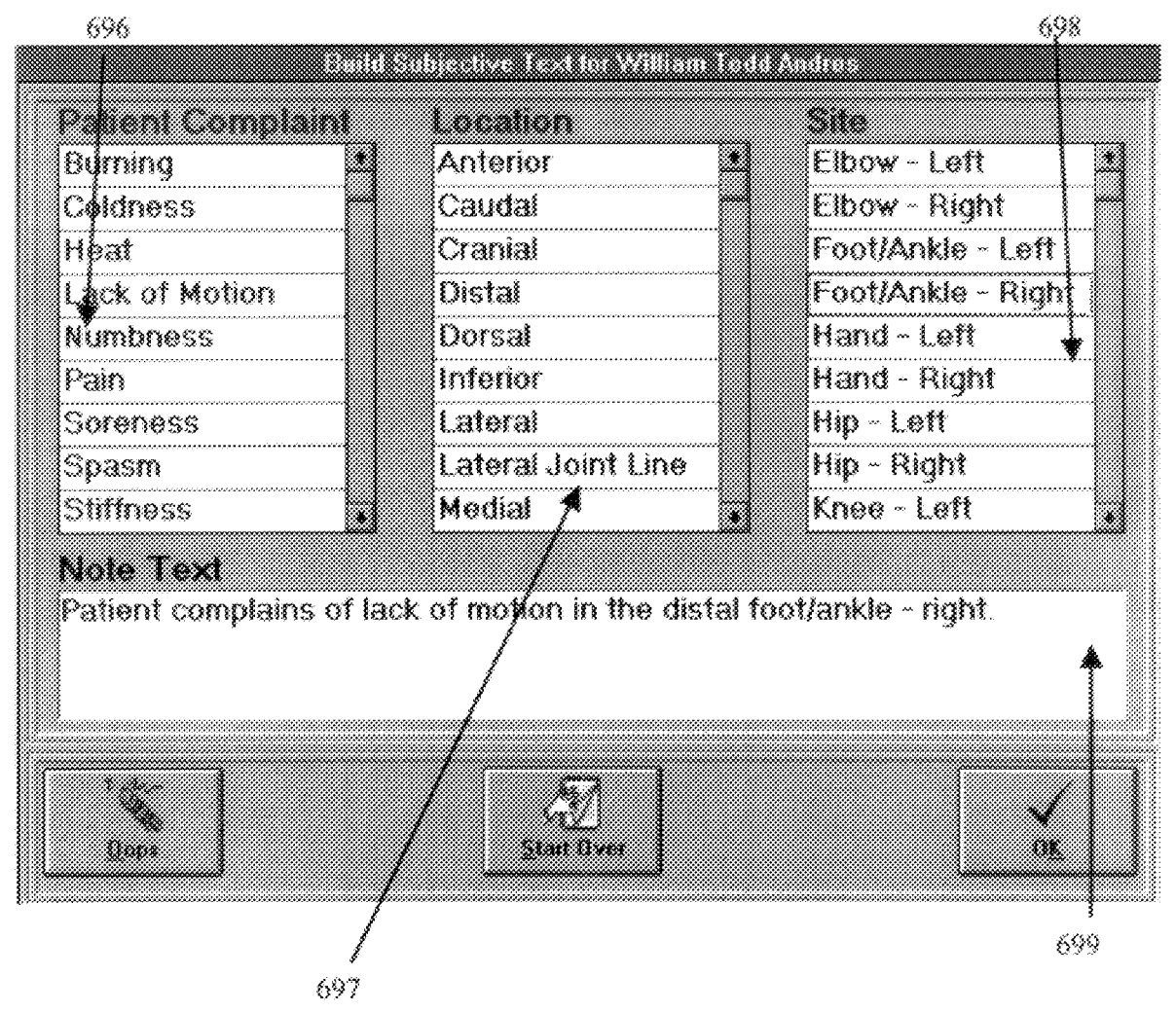

The building of a sentence using multiple, tandem tables of patient rehabilitation data using the Note Builder™ button 617 is shown in FIG. 16a–d. This function allows the user to rapidly enter multiple pieces of data. The Note Builder™ button 617 is pressed to present the screen shown in FIG. 16a. The computer can be programmed by the therapy provider to display any desired combination of tables, and any data fields in those tables. In FIG. 16, for example, the selected tables are for patient complaints 696, location 697, and site 698. The therapy provider scrolls through each table and enters the appropriate patient complaint from the table 696, the appropriate location from the table 697, and the appropriate site from the table 698. The complete text that is constructed by the computer is displayed in a Note Text window 699. After entering the complaint for "lack of motion" from the table 696, the complaint appears in a full text phrase in the area 699 (FIG. 16b). After selecting a location from the table 697, this data field appears in an additional phrase in the area 699 (FIG. 16c). The therapy provider selects a site from the area 698, and this data field appears in the area 699 (FIG. 16d). A complete sentence is thereby constructed in the note text area 699 by the selection of listings from the tables 696–698. The computer can be programmed to present the data fields selected from the tables in any desired phrase or sentence, or in more than one sentence, depending upon the preferences of the therapy provider.

Figure 17A:
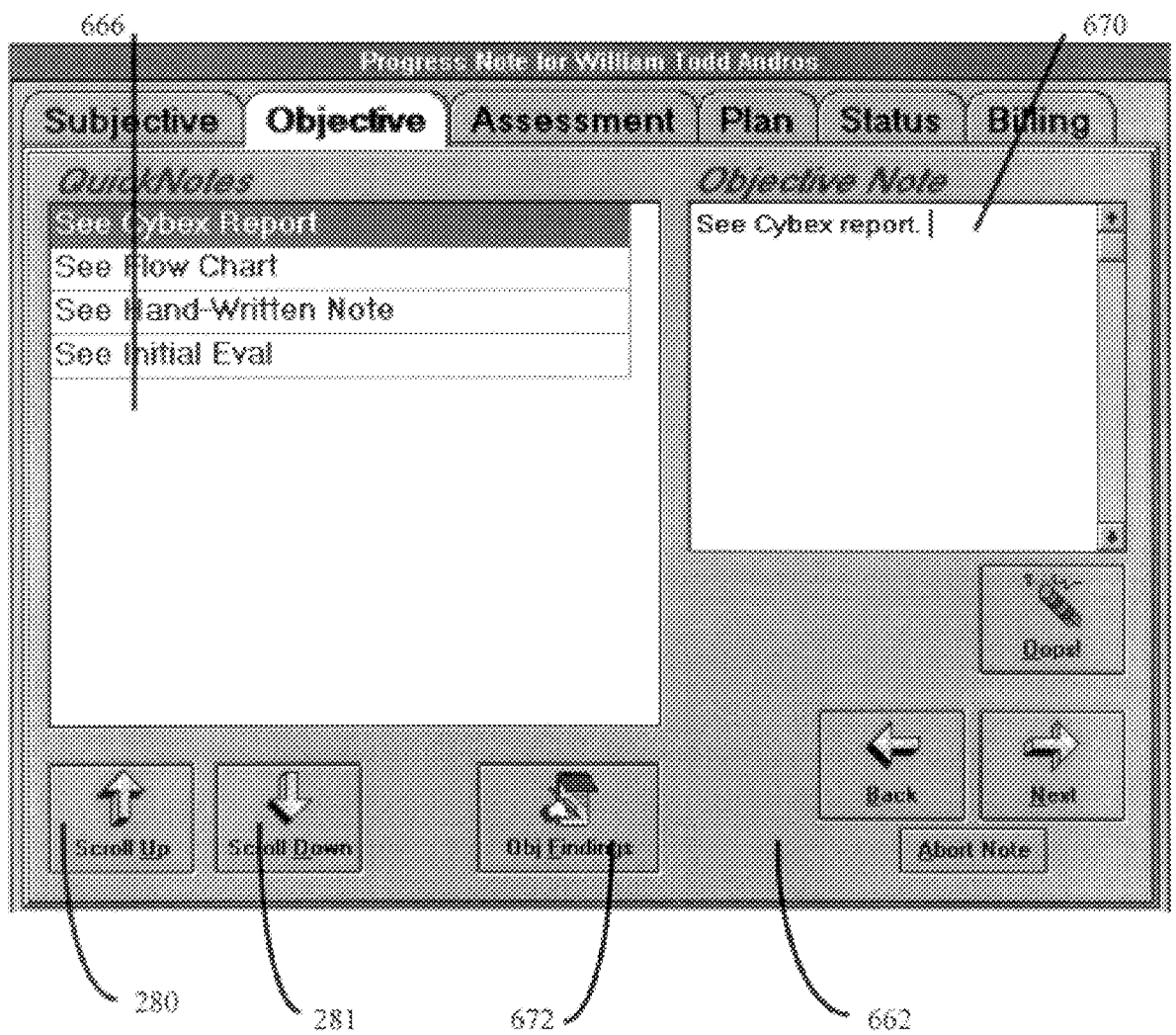
FIGS. 17a–b are progressive screens showing the construction of objective notes for the patient.
Figure 17B:

Objective findings for the patient record are the quantitative results of the therapy session. The Objective screen 662 of the SOAP selections is shown in FIG. 17a–b. This screen 662 includes an area 666 and an area 670. The area 666 lists different records of objective findings. The listings are selected using the scroll up and scroll down buttons 280, 282. The selected data fields can appear in the area 670 (FIG. 17b). The selected data fields of objective findings are displayed in a tabular format by pressing objective findings button 672. The particular objective findings data fields for the therapy session can then be entered by the therapy provider in each of the selected records.

The entry of objective findings data for the therapy session is shown in FIGS. 18 and 19. Listings or abbreviations for appropriate objective measurements of patient progress are shown in the objective findings column 710. The patient's initial measurements can be shown in a column 714. The patient's current measurements can be recorded in a column 718. The ultimate goals for the patient can be displayed in a column 722 to provide the therapy provider with a ready reference of the progress of the patient. The therapy provider moves through the table using the scroll up button 280 and scroll down button 282. Numerical entries are made with the assistance of the keypad screen 620 (FIG. 13). On the completion of the record, a record button 732 is pressed to enter the recorded data fields into memory.

The therapy provider may wish to add or delete objective findings measurements. This can be accomplished by pressing the add objective findings button 736. An Add/Delete screen 740 (FIG. 19) will appear. Common and/or desired objective findings measurements data fields can be provided in a table 744. The therapy provider scrolls through the list using the up and down scroll tabs 80, 81, or the scroll up 280 and scroll down 282 buttons and enters desired objective findings data fields. The objective findings that have been selected preferably appear in a area 746. Selected items can be deleted by selecting the objective finding to be deleted and pressing the remove item button 750. The selected measurements data fields can be entered into memory by pressing an OK tab 754.

Figure 20A:
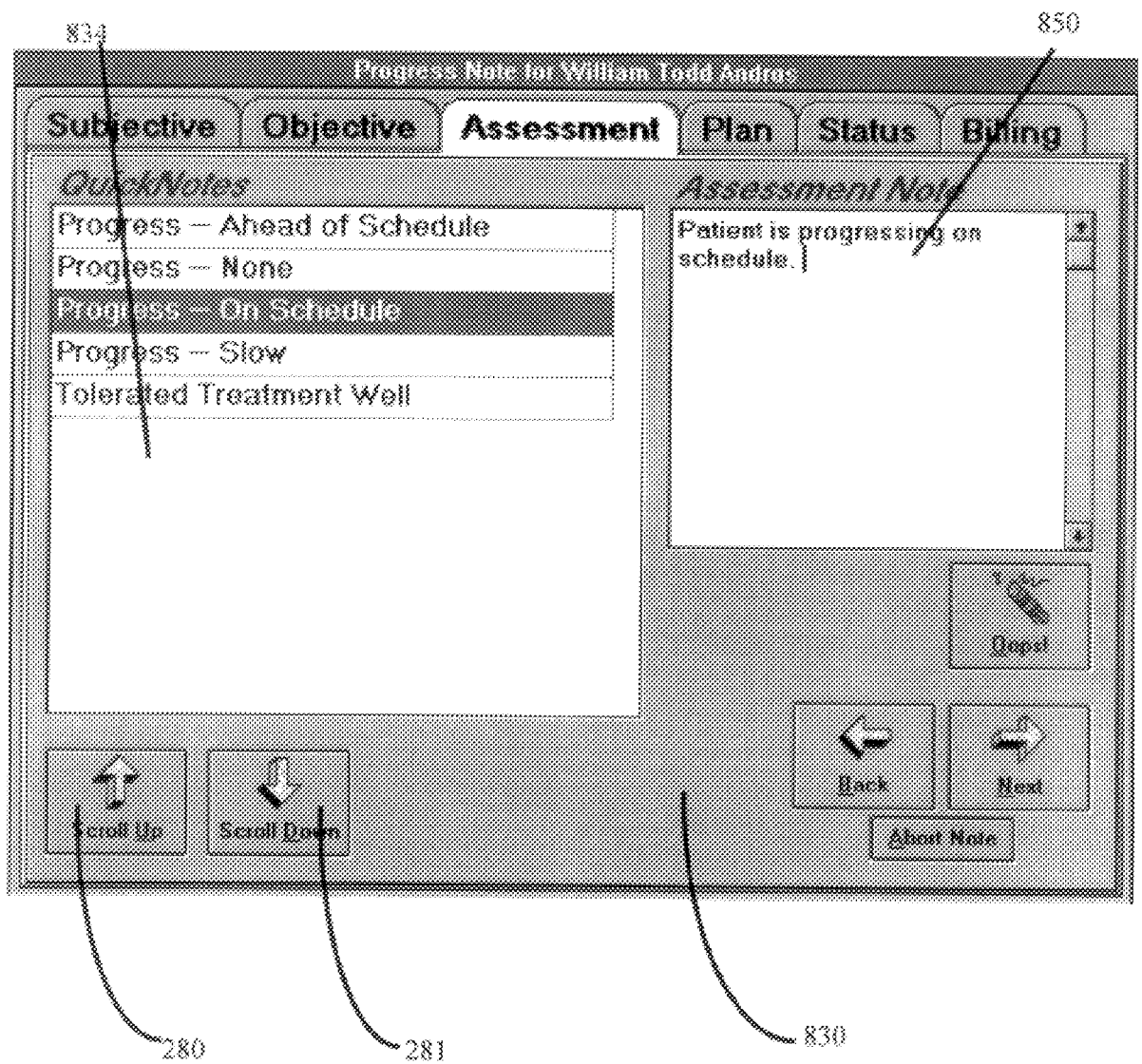
FIGS. 20a–b are screens showing the construction of patient assessment data.
Figure 20B:
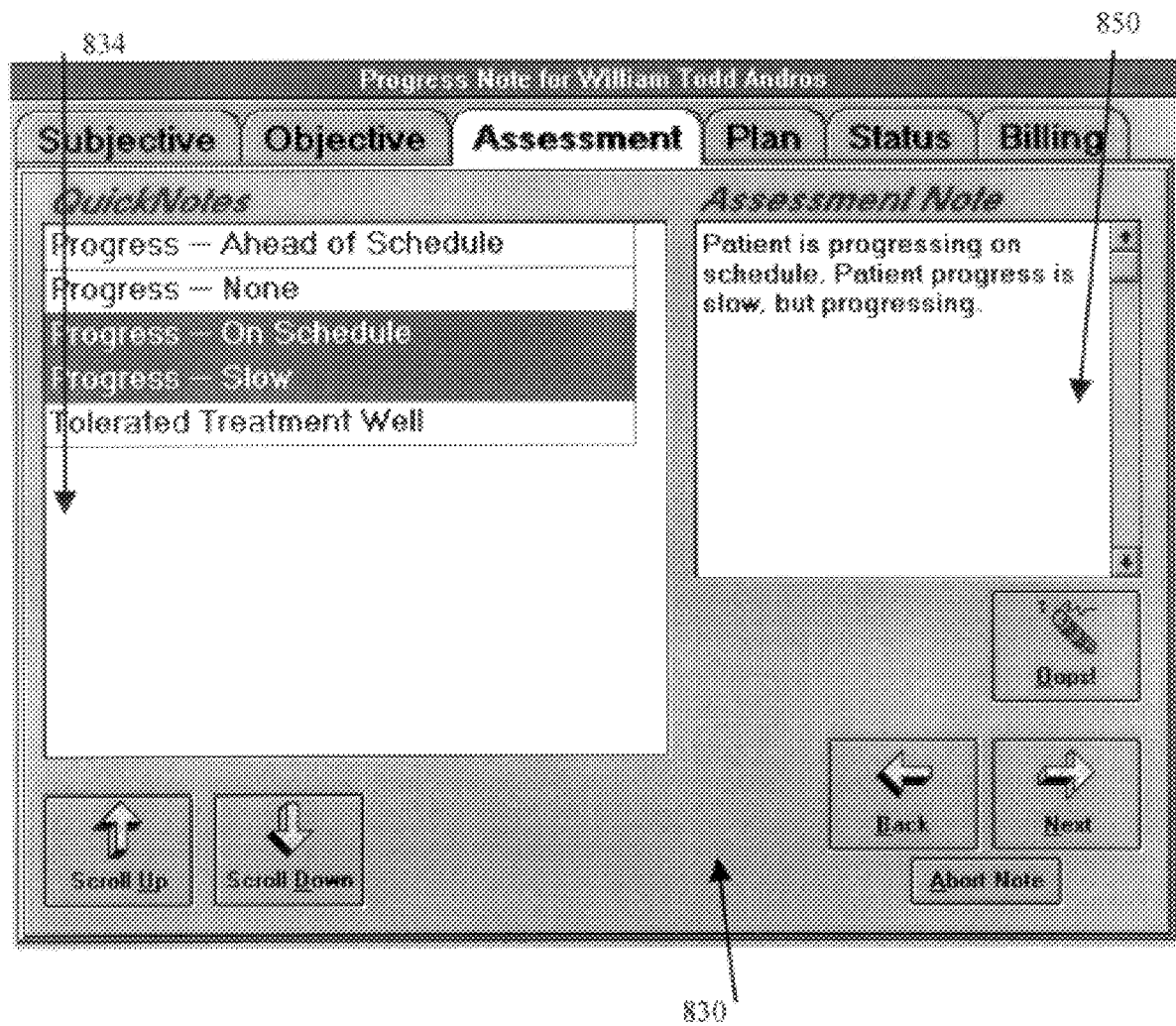

The entry of patient assessment data is shown in FIG. 20a–b. The assessment data characterizes the opinion of the therapy provider as to the status and progress of the patient. The screen 830 includes a selected table of common assessments for patients, shown in the area 834. The appropriate selection is made using the scroll up button 280 and scroll down button 282. Assessment data entered by the therapy provider is matched by the computer with programmed text, and the result appears in the assessment note area 850. Additional text is constructed with the selection of additional assessments (FIG. 20b).

Figure 21A:
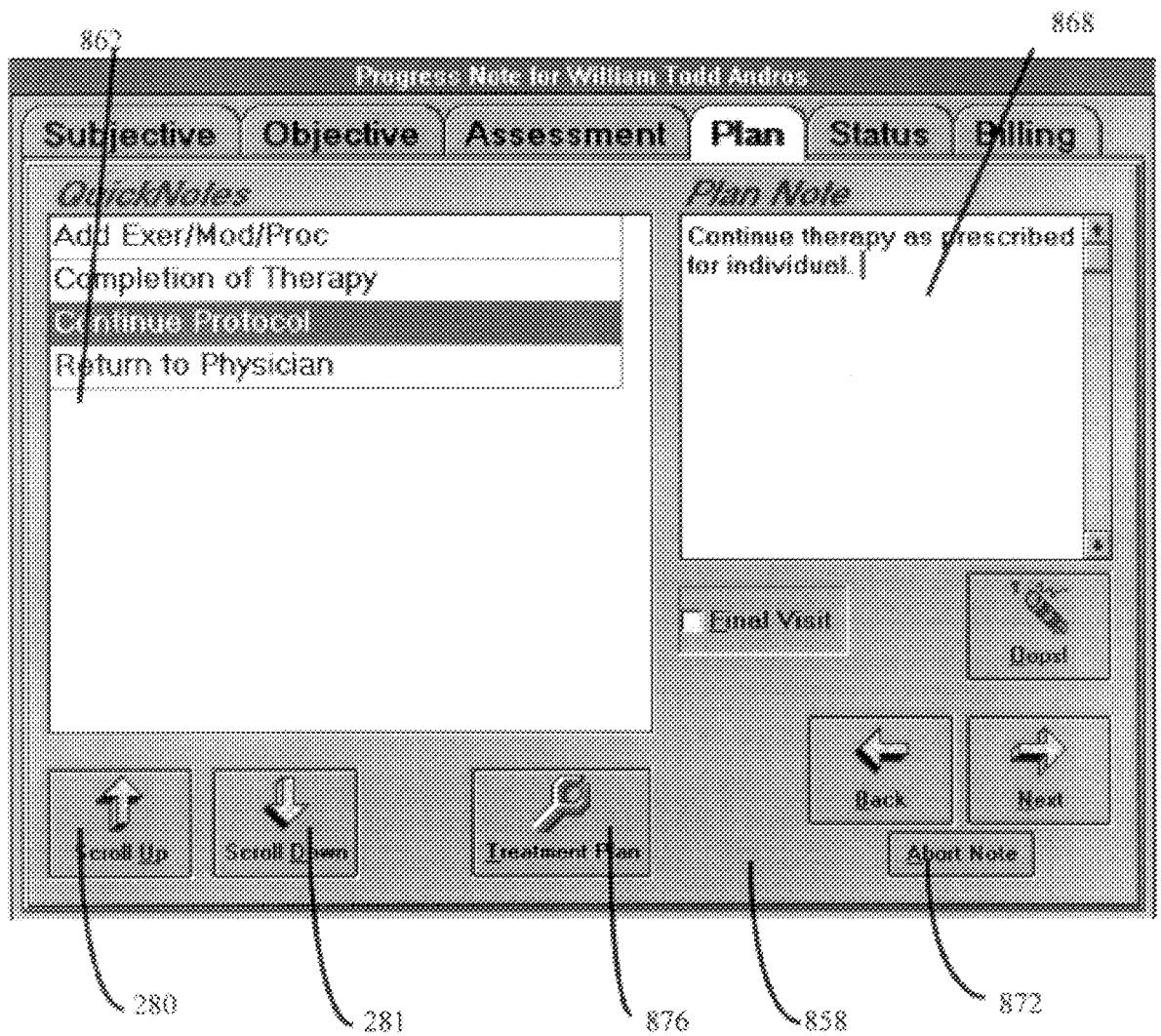
FIGS. 21a–b is a screen showing the construction of patient plan data.
Figure 21B:

The entering of patient plan data fields is shown in FIG. 21a–b. Patient plan data is the future treatment to be administered to the individual patient during the next therapy session. A screen 858 includes an area 862 which lists the recommendation of the therapy provider for future treatment. Listings or abbreviations for possible alternatives are tabularized as data fields in the area 862. The therapy provider can scroll using the scroll up 280 and scroll down 282 buttons to enter appropriate plan selections. The plan selections are combined with predefined phrases, and are displayed as a phrase or a complete sentence in the area 868. Additional text will be created upon the selection of additional listings (FIG. 21b). The note can be aborted using a button 872. The last visit of the patient is indicated by selecting the final visit button 878, which removes the patient's name from the listing of active patients 476 (FIG. 6) and allows the therapy provider to review the goals of the therapy to indicate which of the goals have been met.

Figure 22:
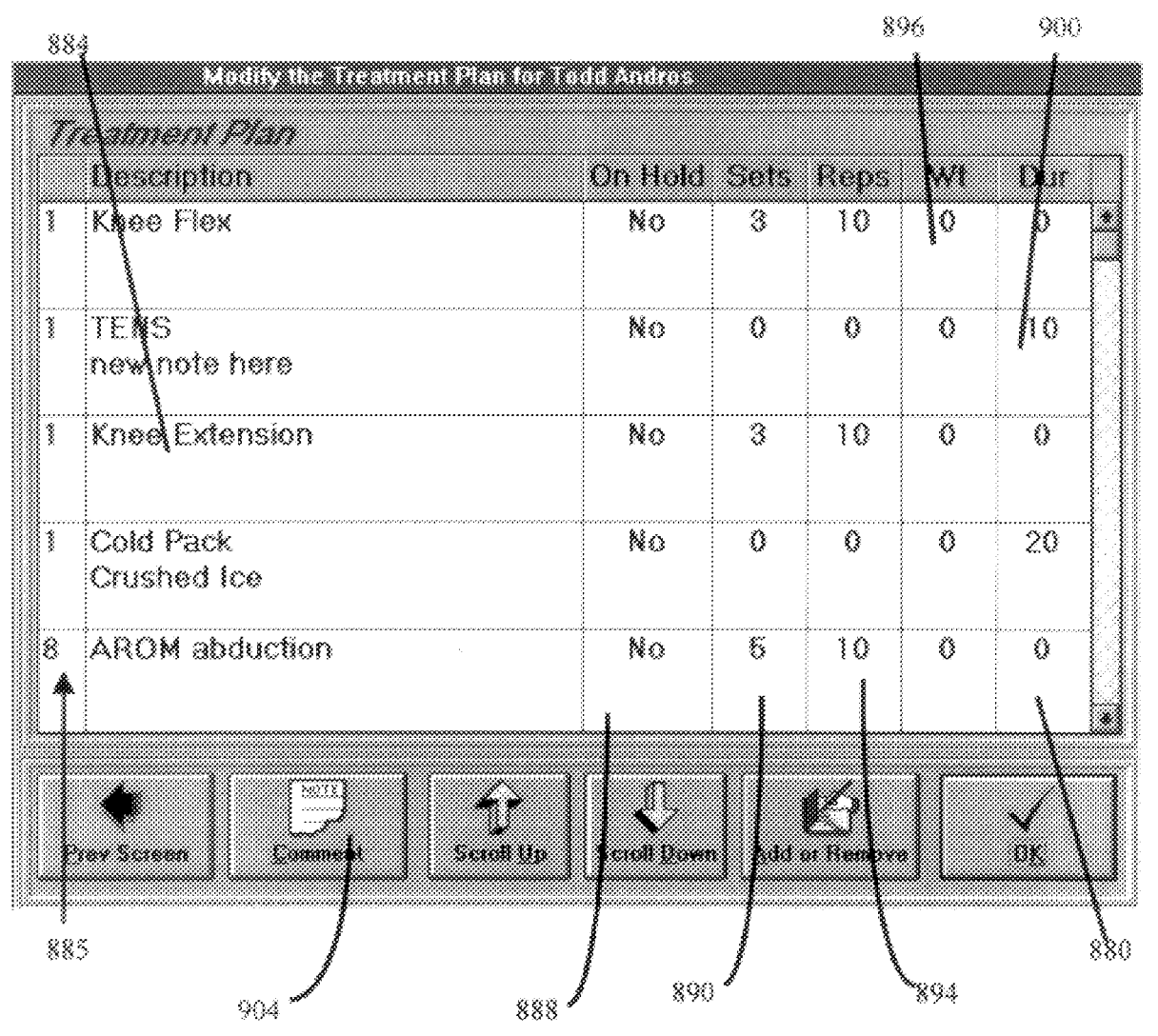

The therapy provider may wish to modify the treatment plan for a patient, for example, as a result of patient performance during a therapy session. The treatment plan is the exercise and modalities that constitute the therapy for an individual patient. Modification of the treatment plan can be made by pressing the treatment plan button 876. The treatment plan screen 880 shown in FIG. 22 will appear. A list of all of programmed treatments for this individual patient is shown in a description table 884. Another column 888 indicates whether the treatment is "on hold" or not to be performed. Other columns show sets 890, repetitions 894, weight 896 and duration 900. A comment button 904 can be used to type in, with an alpha numeric keyboard, specific comments that are particular to the patient which the therapy provider wishes to add to the description column 884. These comments can include seat and weight adjustments, characteristics of the patient, and the like. The order in which specific treatments will appear in column 884 can be changed by placing an appropriate numerical indication of the desired order in the column 885.

Figure 23:
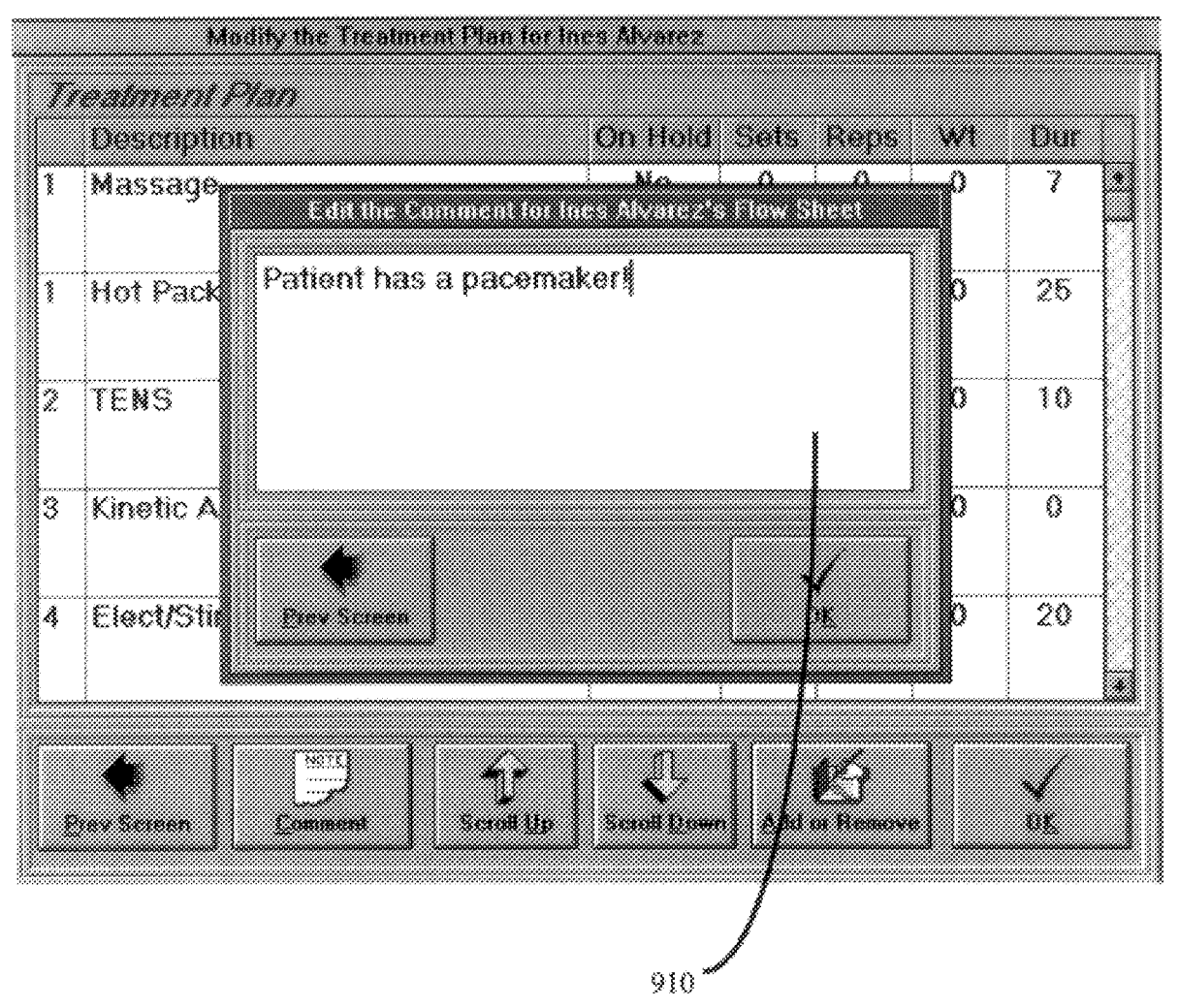
Figure 24:
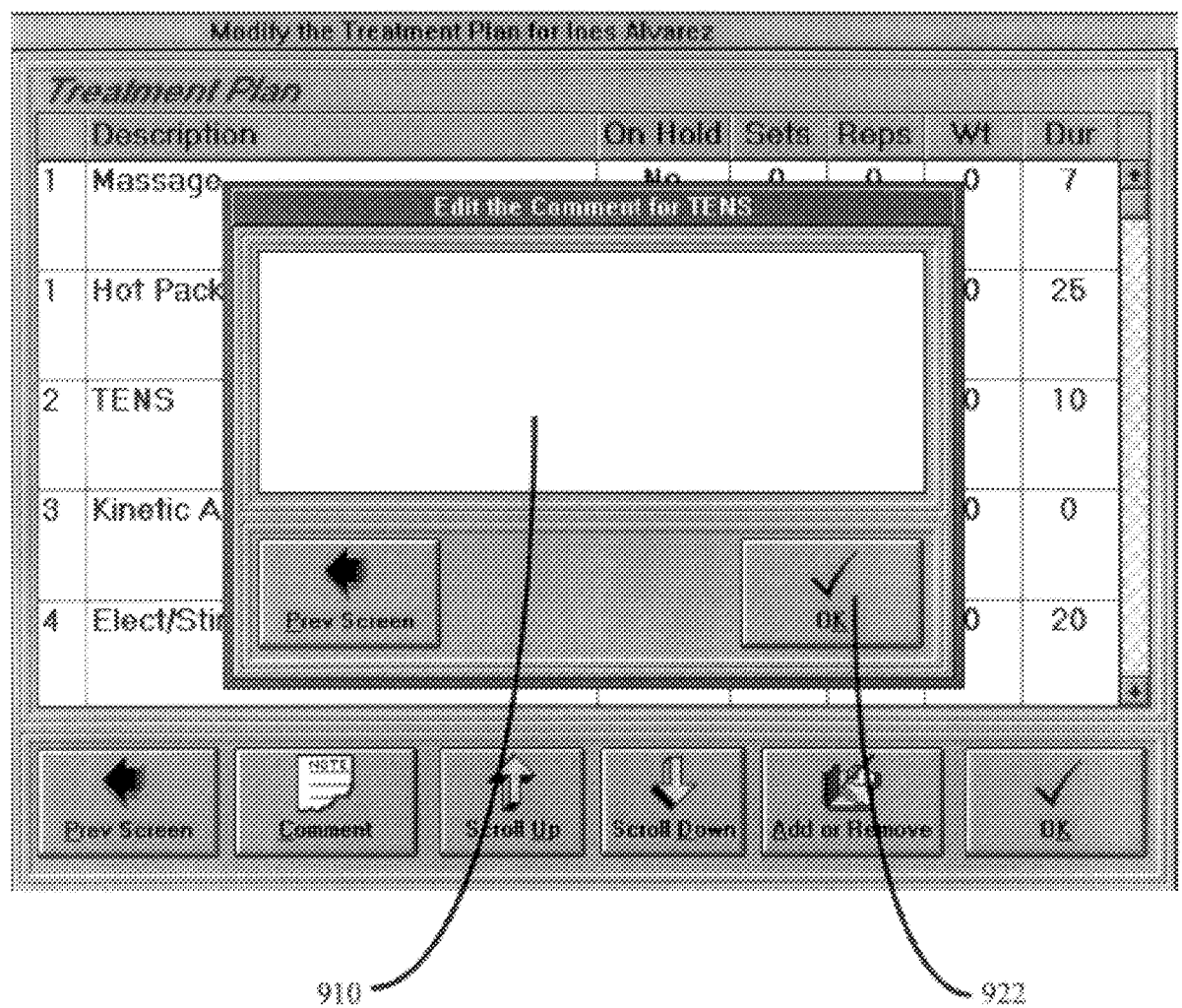

Editing the comments for the treatment plan is shown in FIGS. 23 and 24. Upon entering the description column, and pressing the comment button 904, a text area 910 appears. The desired text is typed on an alpha-numeric keyboard (not shown), and is displayed in a blank area 918 (FIG. 24). Upon entering the appropriate text, an OK button 922 can be pressed to enter the text into memory.

Figure 25:
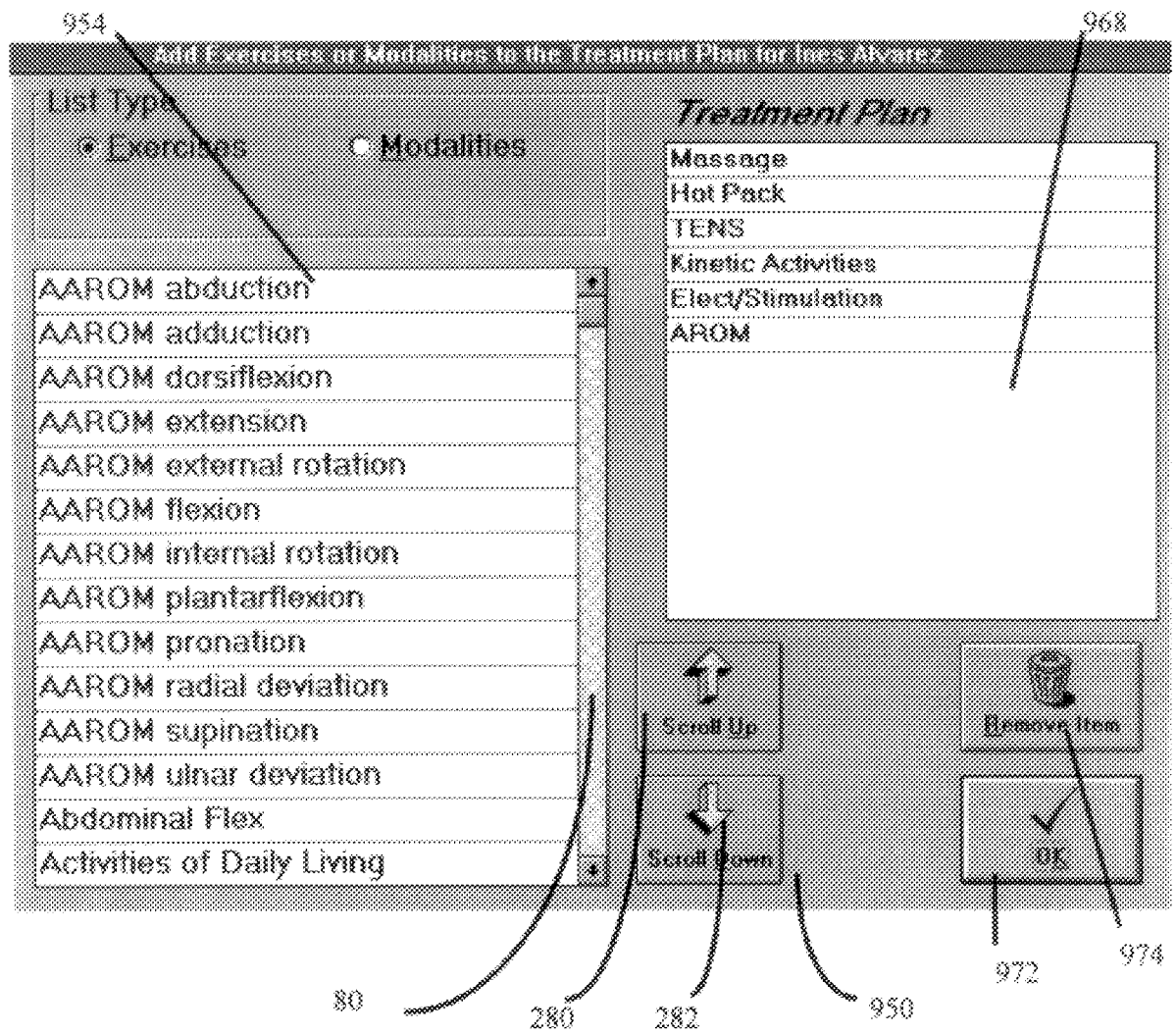
FIG. 25 is a screen showing the addition or deletion of exercises from the treatment plan.

Modification of the treatment plan can be accomplished by pressing the add or remove button 905. This will cause screen 950 of FIG. 25 to appear. Treatment data fields are listed alphabetically by abbreviation or other representations in a table 954. The tabs 80 are used to scroll up and down, as can the scroll up and scroll down buttons 280, 282. The particular treatments that have been selected for the patient are shown in an area 968. When all appropriate treatments for the patient have been selected, an OK button 972 is pressed to enter the data fields into memory. Items can be removed by pressing the remove item button 974.

Figure 26:
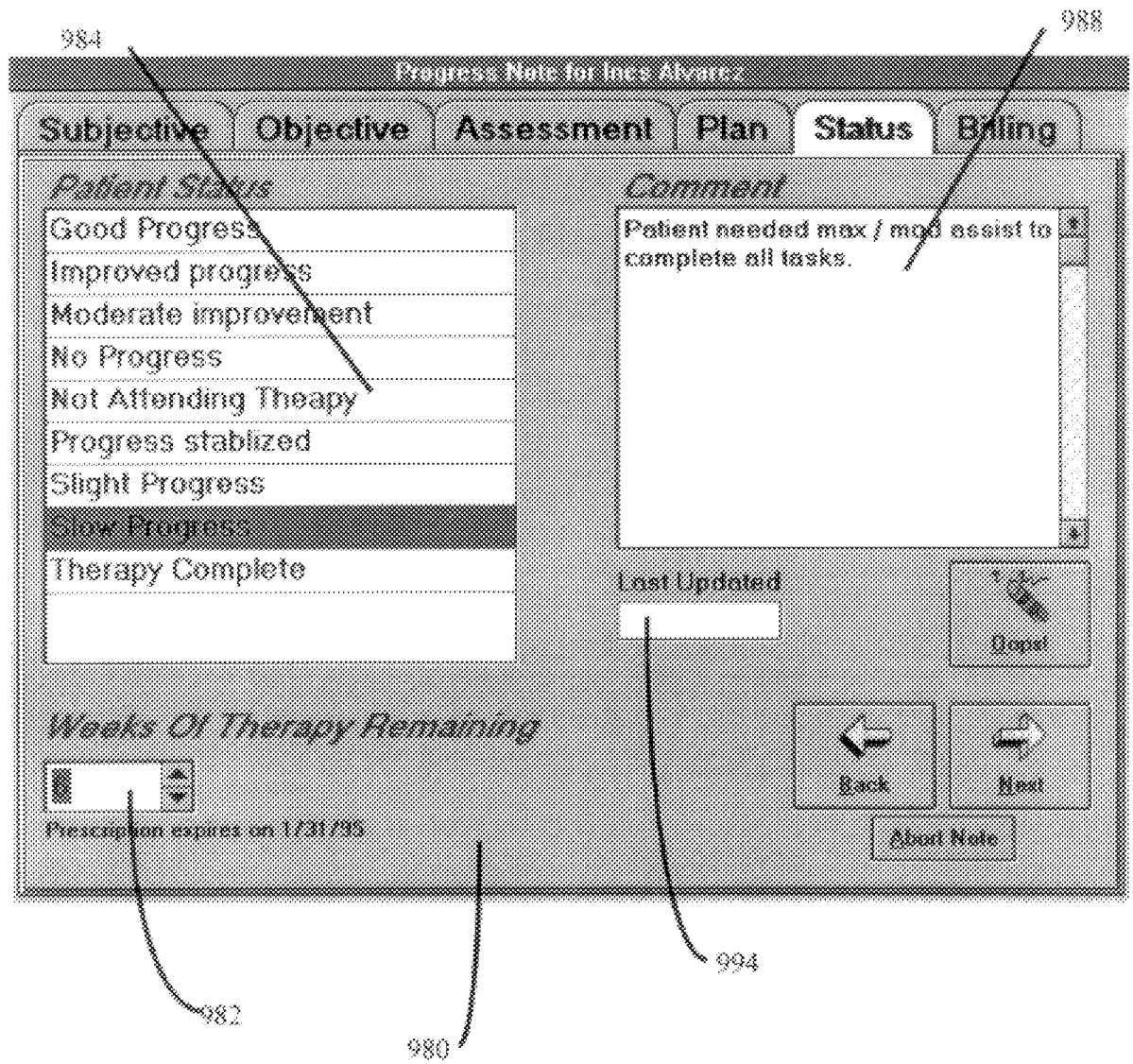
FIG. 26 is a screen showing the entry of status data for the patient.

The entering of patient status data fields is shown in FIG. 26. Patient status data details the status of the patient in the therapy process. A table containing representative indication data fields of common patient status findings is shown in the area 984 the screen 980. The therapy provider selects the appropriate description. The computer matches the selected listings with predefined phrases to create a textual comment that is displayed in area 988. A display 992 of the weeks of therapy remaining is also provided. The therapy provider can type in additional comments as needed for the individual patient using an alpha numeric keyboard. A last updated area 994 can display the last time the patient status was changed.

After the SOAP entries have been made, it is preferable to create a billing listing for the therapy session. A billing screen is preferably provided. A currently preferred screen 1000 is shown in FIG. 27. Billing data fields, including insurance reference numbers, are shown as tabularized lists in an area 1004. The user scrolls using the buttons 80, 81 or scroll up 282 or scroll down 280 buttons. The insurance carrier for the individual patient is preferably displayed in an area 1016. Different carriers require different billing descriptions, sometimes for the same service, and it is therefore helpful to the therapy provider to have this data at the time the billing entry is made. The billing items data fields that are selected are displayed in an area 1020 of the computer screen. Items can be removed using a remove item button 1024, and a note can be erased completely with an abort note button 1026.

Figure 28A:
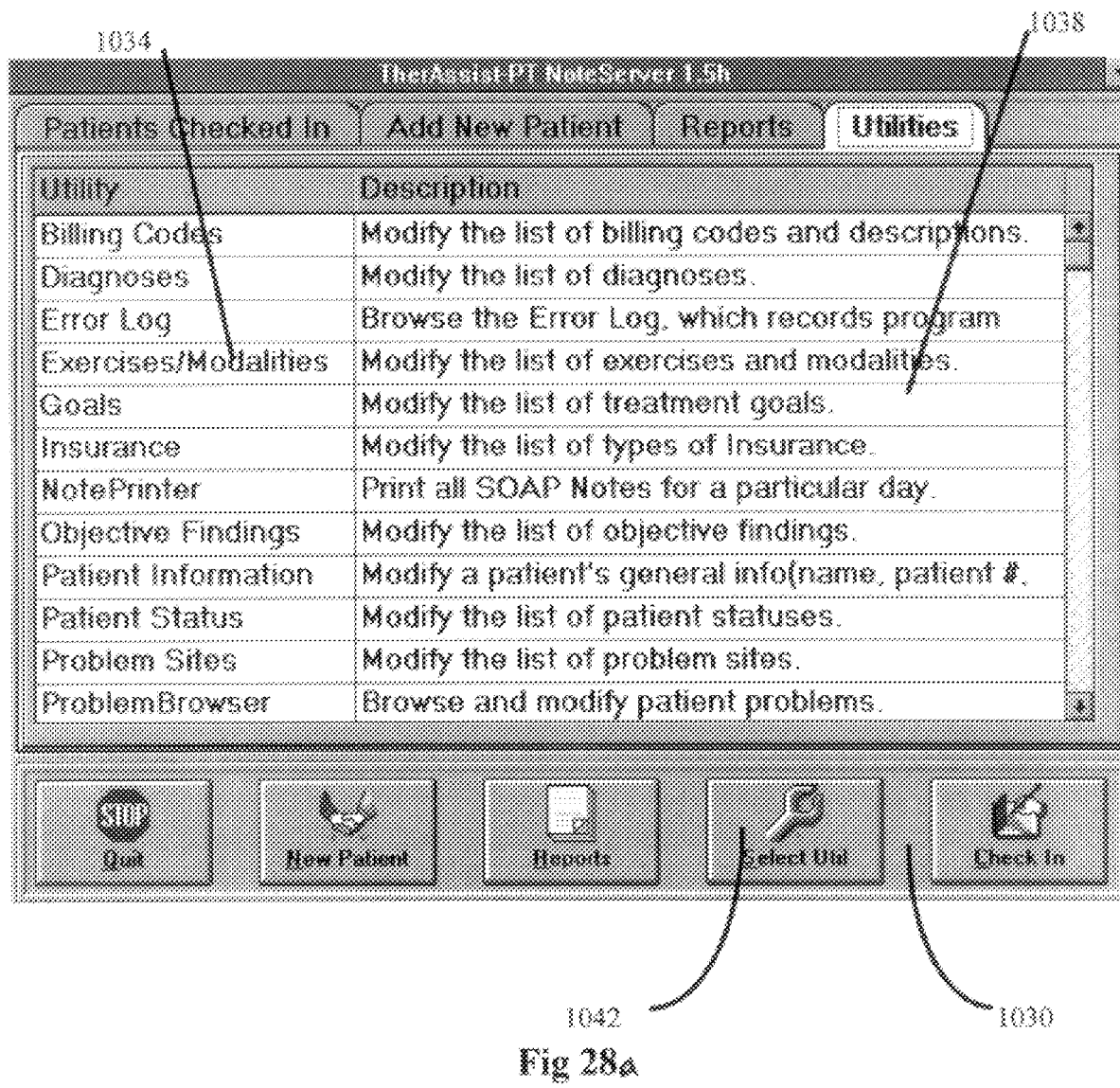
FIGS. 28a–b are progressive screens showing the modification of patient rehabilitation data in the system.
Figure 28B:

The system preferably allows the therapy provider to change almost any of the patient rehabilitation data stored in the system. This is done with a utilities procedure. A utilities screen 1030 is shown in FIG. 28. The screen includes a tabularized list of utilities in an area 1034 from which the therapy provider can select the target area of data that is to be changed. Each listed utility represents a table of records consisting of data fields. The description of the change that is to be made is included in an area 1038 of the screen. The selection of appropriate utility is made with the select utility button 1042. The selected table of all items in the selected category will appear on a screen 1044 (FIG. 28b), where they can be edited by the therapy provider with the use of an alpha numeric keyboard. The lists as edited will be used for all patients.

Figure 29:
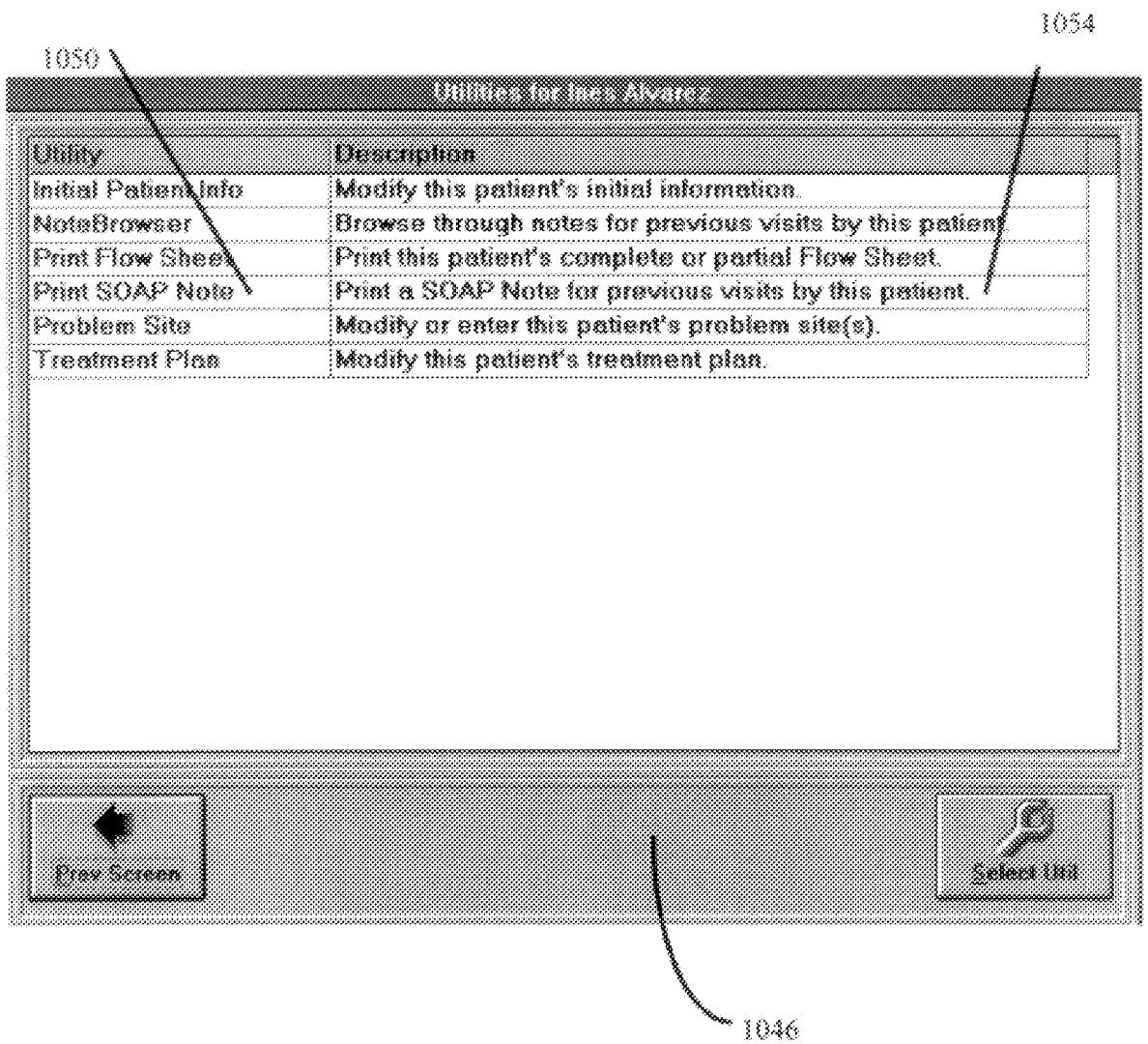
FIG. 29 is a screen showing the modifiable individual patient data.

The utilities for a particular patient are shown in FIG. 29. The patient screen 1046 includes a list of utilities available for the patient shown in an area 1050 of the screen, and description of these utilities that is shown in an area 1054 of the screen. These utilities allow the therapy provider to edit and/or print data in a individual patient file.

Figure 31:
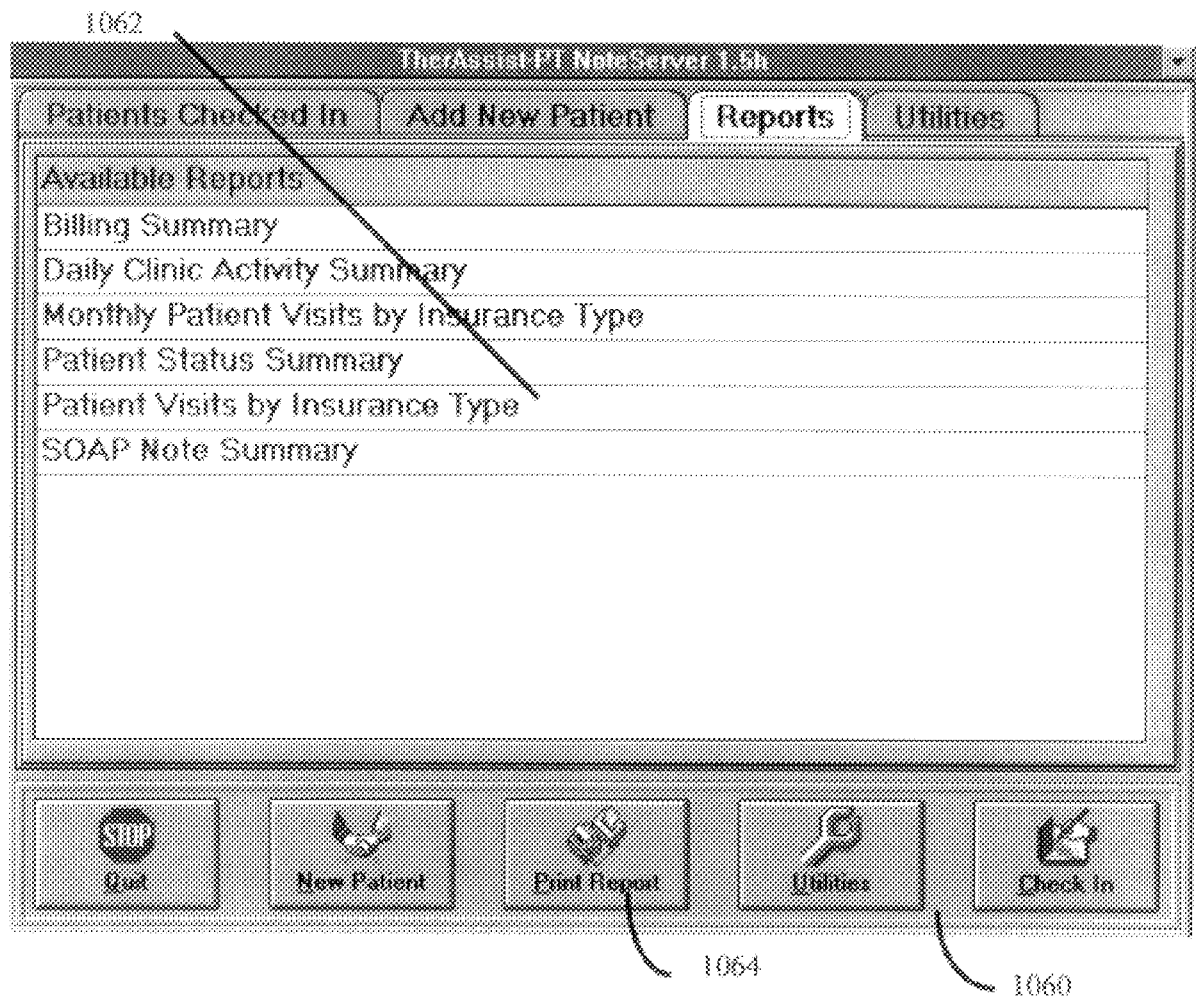
FIG. 31 is a screen showing a brief listing possible patient reports.

After data for the therapy session has been entered, a daily report is preferably automatically generated. An example of an automatically generated report is shown in FIG. 30. The computer can be programmed to generate reports automatically for any desired data field in the patient record. Reports can also be generated manually. A report generation screen 1060 is shown in FIG. 31. Categories of reports can be selected from the area 1062, and the corresponding data will be printed. Reports can be printed using a print report button 1064. The reports generated by the program can be sent by the server 16 through a modem 28 or fax 30 to any desired location, such as the attending physician. In this manner, the attending physician will have an immediate report as to the status of the patient. Also, the report can be printed at the printer 24 to provide a printed copy of the results of the therapy session to be stored in patient files. Alternatively, the report can be recorded in a memory as controlled by the server 16.

The invention is an application program written for the MS Windows operating system, a product of Microsoft Corporation, of Redmond, Wash. The principles of the invention can be applied to different operating systems. The invention can be written using any of a number of software languages. The invention initially written with MS Visual Basic, a product of Microsoft Corporation of Redmond, Wash. The flow sheets of the invention were created with Spread/VBX software, a product of FarPoint Technologies, of Morrisville, N.C. The tabs of the invention were created with VSVBX software, a product of VideoSoft of Berkeley, Calif. The reports of the invention were created with Crystal Reports software, a product of Crystal Reports, of Vancouver, BC Canada.

The invention can take other specific forms without departing from the sprit or essential attributes thereof, and reference should therefore be made to the following claims rather than to the foregoing specification, as indicating in the scope thereof.

We claim:

1. In a computer system, a method for assisting administration and monitoring of the therapy of patients, the method comprising:
   storing patient individual rehabilitation data records in a memory in the computer system;
   retrieving and updating a patient individual data record in said memory of said computer system for a selected patient upon arrival of said selected patient for a therapy activity;
   operating the computer system to generate at least one therapy session input screen corresponding to the selected patient, said therapy session input screen being generated for the therapy provider for use in administering therapy to said patient, said therapy session input screen showing treatments to be administered to said patient during a therapy session, and said patient individual data record including patient activity data from previous therapy sessions;
   inputting subjective data into said therapy session input screen in said computer system by the therapy provider selecting choices from lists of subjective data fields; and
   recording said selected data fields in said computer system by entering said data fields into said computer memory wherein said at least a portion of said patient data is displayed as a list and;
   retrieving predefined phrases for said patient data, storing and combining said patient data with said phrases when said data is selected from the said list for creating a therapy report.

2. The method of claim 1, wherein said set of patient rehabilitation data comprises patient symptom data.

3. The method of claim 2, wherein the patient symptom data comprises patient complaint data and site data.

4. The method of claim 3, wherein said site data comprises body part data and at least one of lateral and medial location data.

5. The method of claim 1, wherein said representations comprise abbreviations for said patient rehabilitation data, said patient rehabilitation data being stored upon selection of the corresponding abbreviation.

6. The method of claim 5, wherein said selection is made by one selected from the group consisting of touch screen, mouse, computer pen and an alpha-numeric data entry device.

7. The method of claim 1, wherein said selected patient data is displayed in at least a partially blank text area on a computer screen.

8. The method of claim 1, further comprising the step of providing at least one reception computer and at least one remote computer, the remote computer being networked to the reception computer, whereby patient rehabilitation data can be communicated between said computers.

9. The method of claim 8, wherein said reception computer is used to provide access to a list of patients, selection of a patient name permitting the retrieval from a memory patient rehabilitation data including the names of therapy providers.

10. The method of claim 9, wherein a therapy provider is provided with a remote computer, selection of the name of the therapy provider retrieving the patient file and sending said file to said remote computer and providing an indication at said remote computer that said patient has arrived for therapy.

11. The method of claim 9, wherein selection of a patient name retrieves patient rehabilitation data including a therapy treatment plan for said patient, said therapy treatment plan being sent to a printer to produce a printed copy of said treatment plan for use by the therapy provider for the therapy session with said patient.

12. The method of claim 1, wherein at least a portion of said patient rehabilitation data entered during a therapy session is sent to a printer to produce a printed report of the results of the therapy session.

13. The method of claim 12, wherein said patient rehabilitation data sent to the printer includes patient subjective, objective, assessment and plan data for said therapy session.

14. The method of claim 1, wherein said patient rehabilitation data includes patient status data.

15. The method of claim 14, wherein said patient status data includes at least one of patient condition, time remaining in therapy, and patient notes entered by the therapy provider.

16. The method of claim 15, wherein said patient status data is sent to a printing device to produce a printed status report.

17. The method of claim 16, wherein said printing device is a facsimile device.

18. The method of claim 1, wherein at least a portion of said representations are displayed as a list of options in a portion of said computer screen, said therapy provider selecting from said options, said selected options being displayed in another portion of a computer screen.

19. The method of claim 18, wherein said options are selected from exercises, modalities, and objective findings.

20. The method of claim 18, wherein said listed options are edited by said therapy provider for the particular characteristics and status of the patient.

21. The method of claim 1, wherein said patient rehabilitation data comprises patient problem site, diagnosis, and treatment goals data entered by said therapy provider during the initial treatment session with said patient.

22. The method of claim 1, wherein patient billing data is displayed as a list of options, said therapy provider selecting from the list of options to generate patient billing data for the therapy session.

23. The method of claim 22, wherein insurance carrier data for said patient is provided to permit the selection of billing data for appropriate said carrier.

24. The method of claim 22, wherein said selected billing data for said therapy session is sent to at least one of a data storage device, a printer, and an electronic transmission device.

25. The method of claim 1, further comprising:
   generating a printed output report summarizing patient activity occurring during the present therapy session.

26. The method of claim 25, further comprising:
   generating a billing statement in response to the data entered into the therapy session input screen and in response to billing data stored in memory of the computer system.

27. A computer system for assisting administration and monitoring the therapy of patients, the method comprising:
   means for storing patient personal rehabilitation data records in the computer system;

means for updating a patient personal data record for a selected patient in said memory of said computer system upon arrival of said selected patient for therapy activity;

means for generating a therapy session input screen corresponding to the selected patient, said therapy session input screen being generated for the therapy provider for use in administering therapy to said patient, said therapy session input screen showing treatments to be administered to said patient during a therapy session, and said therapy record showing patient activity data from previous therapy sessions;

means for displaying lists of choices of subjective therapy data to the therapy provider in association with said therapy session input screen, to assist input of data to record therapy activity;

means for selecting choices from the lists of subjective therapy data to record patient activity during a present therapy session;

means for entering said subjective therapy data to record patient activity during the therapy session to provide a record of patient activity during the present session.

means for automatically combining said selected therapy data with predefined phrases thereby creating a patient report.

28. The computer system of claim 27, further comprising:

means for generating a printed output report summarizing patient activity occurring during the present therapy session.

29. The method of claim 27, further comprising:

means for generating a billing statement in response to the data entered into the therapy session input screen and in response to the billing rates stored in memory of the computer system.

30. A method for operating a programmable computer to facilitate the rehabilitation of patients and the documentation of said rehabilitation, comprising the steps of:

defining at least one field of patient rehabilitation data;

defining visual representations for each of said patient rehabilitation data;

displaying said representations on a computer screen;

providing means to permit a therapist to select at least one of said representations;

defining a sentence phrase for said field of patient rehabilitation data;

selecting at least one of said representations on said computer screen;

storing the corresponding patient data and sentence phrase in response to the selection of at least one of said representations according to said definition of said sentence phrase for said field of patient rehabilitation data; and combining a set of said patient rehabilitation data and said phrases to generate a patient therapy report.

31. A method for operating a programmable computer to facilitate the rehabilitation of patients and the documentation of said rehabilitation, comprising the steps of:

defining at least one field of patient rehabilitation data;

defining visual representations for each of said patient rehabilitation data in said field;

displaying said representations on a computer screen;

providing means for selecting said representations;

providing means responsive to said selection for entering said selected data into a computer memory, said means comprising at least one selected from the group consisting of;

(a) displaying a numeric keypad on said computer screen for entering numerical patient data;

(b) displaying at least a partially blank text entry area on said computer screen, said area displaying text entered by the user on an alpha-numeric data entry device;

(c) displaying in sequential fashion responsive to said selection predefined alternatives, whereby the user can continue the selection process until the desired alternative appears; and storing patient rehabilitation data entered in said memory combining said patient rehabilitation data with predefined phrases for creating a therapy report.

32. A system for providing rehabilitation to patients and the documenting said rehabilitation, comprising;

at least one programmable computer having a memory;

at least one data field of said patient information data stored in said memory;

at least one visual representation for one of said patient rehabilitation data stored in said memory;

means for displaying at least one of said patient rehabilitation data and said representations on a computer screen;

means for selecting at least one of said displayed visual patient rehabilitation data and representations; and, means for storing the patient data in response to the selection of at least one of said patient rehabilitation data and representations;

means for automatically combining said selected patient data with predefined phrases thereby creating a patient report.

33. The system of claim 32, further comprising predefined phrases for said patient data stored in said memory, and means for recalling said phrases upon selection of said data and representations.

34. The system of claim 33, wherein said representation comprise said abbreviations and symbols for said patient rehabilitation data.

35. The system of claim 33, wherein said means for selecting is at least one selected from the group consisting of a touch screen, mouse, computer pen, alpha numeric data entry device.

36. The system of claim 33, further comprising at least one reception computer and at least one remote computer, the remote computer being connected to the reception computer, whereby patient rehabilitation data can be communicated between said computers.

37. The system of claim 36, further comprising means for retrieving patient rehabilitation data and sending said data to said remote computer, and means for providing an indication at said remote computer that a patient has arrived at therapy.

38. The system of claim 33, further comprising a printer, a portion of said patient rehabilitation data comprising patient therapy treatment plan data, and means for sending to said printer said therapy treatment plan for producing printed copy of said treatment plan for use by the therapy provider for a therapy session with said patient.

39. The system of claim 33, further comprising at least one defined data field of said patient rehabilitation data, and means responsive to said selection for entering data in said data field.

40. The system of claim 39, wherein said means for entering comprising at least one selected from the group consisting of a numeric keypad on said computer screen for entering numerical data, an alpha numeric data entry device, and a sequential display of predefined alternatives.

* * * * *